(12) United States Patent
Lai et al.

(10) Patent No.: US 10,960,041 B2
(45) Date of Patent: Mar. 30, 2021

(54) **METHOD FOR ALLEVIATING ULTRAVIOLET DAMAGE WITH ETHYL ACETATE-EXTRACTED PRODUCT OF *SEDUM FORMOSANUM***

(71) Applicant: ESEN BIOTECH INC., Irvine, CA (US)

(72) Inventors: I-Cheng Lai, Taichung (TW); Alicia Lai, Taichung (TW); Heng-Ju Lai, Taichung (TW)

(73) Assignee: ESEN Biotech Inc., Irvine, CA (US)

( * ) Notice: Subject to any disclaimer, the term of this patent is extended or adjusted under 35 U.S.C. 154(b) by 135 days.

(21) Appl. No.: 16/470,365

(22) PCT Filed: Nov. 2, 2018

(86) PCT No.: PCT/US2018/058881
§ 371 (c)(1),
(2) Date: Jun. 17, 2019

(87) PCT Pub. No.: WO2019/090035
PCT Pub. Date: May 9, 2019

(65) Prior Publication Data
US 2019/0328812 A1 Oct. 31, 2019

(30) Foreign Application Priority Data

Nov. 6, 2017 (TW) .................................. 106138254

(51) Int. Cl.
| | | |
|---|---|---|
| *A61K 36/00* | (2006.01) | |
| *A61K 36/41* | (2006.01) | |
| *A61K 9/00* | (2006.01) | |
| *A61P 17/00* | (2006.01) | |
| *A61K 8/9789* | (2017.01) | |
| *A61Q 19/00* | (2006.01) | |
| *A61K 47/20* | (2006.01) | |
| *A61K 9/08* | (2006.01) | |
| *A61K 47/10* | (2017.01) | |
| *A61Q 19/08* | (2006.01) | |

(52) U.S. Cl.
CPC ............ *A61K 36/41* (2013.01); *A61K 8/9789* (2017.08); *A61K 9/0014* (2013.01); *A61K 9/0019* (2013.01); *A61K 9/0053* (2013.01); *A61K 9/08* (2013.01); *A61K 47/10* (2013.01); *A61K 47/20* (2013.01); *A61P 17/00* (2018.01); *A61Q 19/004* (2013.01); *A61Q 19/08* (2013.01); *A61K 2236/33* (2013.01)

(58) Field of Classification Search
None
See application file for complete search history.

(56) References Cited

U.S. PATENT DOCUMENTS

| | | |
|---|---|---|
| 2007/0122492 A1 | 5/2007 | Behr et al. |
| 2010/0040709 A1 | 2/2010 | Mitra et al. |
| 2013/0071342 A1 | 3/2013 | Jeon et al. |
| 2017/0007632 A1 | 1/2017 | Lai et al. |

FOREIGN PATENT DOCUMENTS

WO    2012/012390 A1    1/2012

OTHER PUBLICATIONS

Chen, Comparison of Antioxidant Capability after Isopropanol Salting-Out Pretreatment and n-Butanol Partition Extraction, and Identification and Evaluation of Antioxidants of Sedum formosanum N.E.Br. Molecules (Basel, Switzerland), (Apr. 19, 2016) vol. 21, (Year: 2016).*
International Search Report issued in PCT/US2018/058881, dated Jan. 24, 2019 (2 pages).
Office action dated Nov. 6, 2017 for Taiwan report patent application No. 107138831.
English translation of office action dated Nov. 6, 2017 for Taiwan report patent application No. 107138831.
Wang, Yu-Chen. Study review of the Sedum Formosanum Extract-Induced Change of Intracellular Mediators on the Radiation Treatment of Human Prostate Cancer Cells DU145 and the cited references.

\* cited by examiner

*Primary Examiner* — Qiuwen Mi

(57) ABSTRACT

A method for alleviating ultraviolet damage includes administering to a subject in need thereof a composition containing an ethyl acetate-extracted product of *Sedum formosanum*. The ethyl acetate-extracted product of *Sedum formosanum* is prepared by a process including the steps of (a) extracting *Sedum formosanum* with a solution of monohydric alcohol to obtain a alcohol-extracted product from *Sedum formosanum*; (b) partitioning the alcohol-extracted product with water and n-hexane to obtain an aqueous layer and a n-hexane layer; and (c) partitioning the aqueous layer obtained in step (b) with ethyl acetate, followed by collecting an ethyl acetate layer thus formed to obtain the ethyl acetate-extracted product of *Sedum formosanum*.

14 Claims, 13 Drawing Sheets

Normal control group

UV control group

Experimental group

METHOD FOR ALLEVIATING ULTRAVIOLET DAMAGE WITH ETHYL ACETATE-EXTRACTED PRODUCT OF *SEDUM FORMOSANUM*

FIELD

The present disclosure relates to a method for alleviating ultraviolet (UV) damage with a composition containing an ethyl acetate-extracted product of *Sedum formosanum*.

BACKGROUND

Radiation is the emission or transmission of energy in the form of waves or particles through a space or a material medium. In general, radiation is classified as: (1) ionizing radiation, which refers to high-energy electromagnetic waves (e.g., X-rays and gamma rays) or particles (e.g., alpha particles, beta particles and neutrons) capable of ionizing atoms or molecules; and (2) non-ionizing radiation, which refers to low-energy electromagnetic waves (e.g., visible light, infrared, ultraviolet (UV), microwaves and radio wave) not capable of ionizing atoms or molecules. One of the mechanisms causing UV-induced cell damage is mutagenic DNA lesion, through the formation of cyclobutane pyrimidine dimers (CPDs) and 6-4 photoproducts (6,4PPs).

Ultraviolet (UV) damage occurs when any portion of an organism (such as human) is exposed to UV for a sufficiently long period. Symptoms of UV damage include: skin inflammation, delayed tanning reaction, skin aging (also known as photoaging), severe pains in the joints and muscles and around the eyes, shock, fever, nausea, vomiting, generalized weakness, etc., and the formation of tumor or cancer (such as skin cancer) might also be induced eventually.

Drugs used clinically to alleviate UV damage include: topical steroids (such as Chemin ointment), non-steroidal anti-inflammatory drugs (NSAID) (such as ibuprofen and naproxen), anti-histamines (such as cyproheptadine and astemizole) and sunscreens (such as para-amino benzoic acid (PABA), oxybenzone and vitamin A palmitate). However, these drugs might not achieve the desired therapeutic effect and may also cause severe side effects. Therefore, researchers in this field have attempted to identify active components from traditional Chinese medicines that can be used to treat and/or prevent UV damage.

*Sedum formosanum*, also known as *Sedum alfredii* (trivial name: Alfred Stonecrop; fo jia cao in pinyin) is a perennial herb which belongs to the genus *Sedum* and family Crassulaceae. *Sedum formosanum* can be found in Taiwan, Japan, Ryukyu Islands, the Philippines, etc. Studies have indicated that *Sedum formosanum* has anti-inflammation, hypoglycemic and hypolipidemic effects, and can be used to treat diabetes, sore throat, enteritis, dysenteria, etc.

In the Master's thesis completed by Yu-Chen Wang in 2012 while attending the Department of Biotechnology of Hungkuang University (name: The *Sedum formosanum* Extract-Induced Change of Intracellular Mediators on the Radiation Treatment of Human Prostate Cancer Cells DU145), a methanol extract was obtained by extracting the dried and pulverized *Sedum formosanum* with methanol under sonication, then the methanol extract was partitioned with n-hexane, and the resultant aqueous layer was further partitioned with ethyl acetate. The resultant ethyl acetate layer (i.e., ethyl acetate fraction) was found to contain astragalin, vitexin and kaempferol-3-O-malonyl glucoside by High performance liquid chromatography (HPLC) analysis and liquid chromatography-mass spectrometry (LC-MS) analysis. In addition, it was shown that the ethyl acetate fraction can inhibit the growth of prostate cancer cells DU145, but also can protect DU145 from ionizing radiation-induced cell apoptosis.

As far as the inventors are aware, there have been no documents or prior art patents which disclose that an ethyl acetate-extracted product of *Sedum formosanum* can be utilized in the alleviation of UV damage.

SUMMARY

Therefore, an object of the disclosure is to provide a method for alleviating UV damage that can alleviate at least one of the drawbacks of the prior art.

The method includes administering to a subject in need thereof a composition containing an ethyl acetate-extracted product of *Sedum formosanum*.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
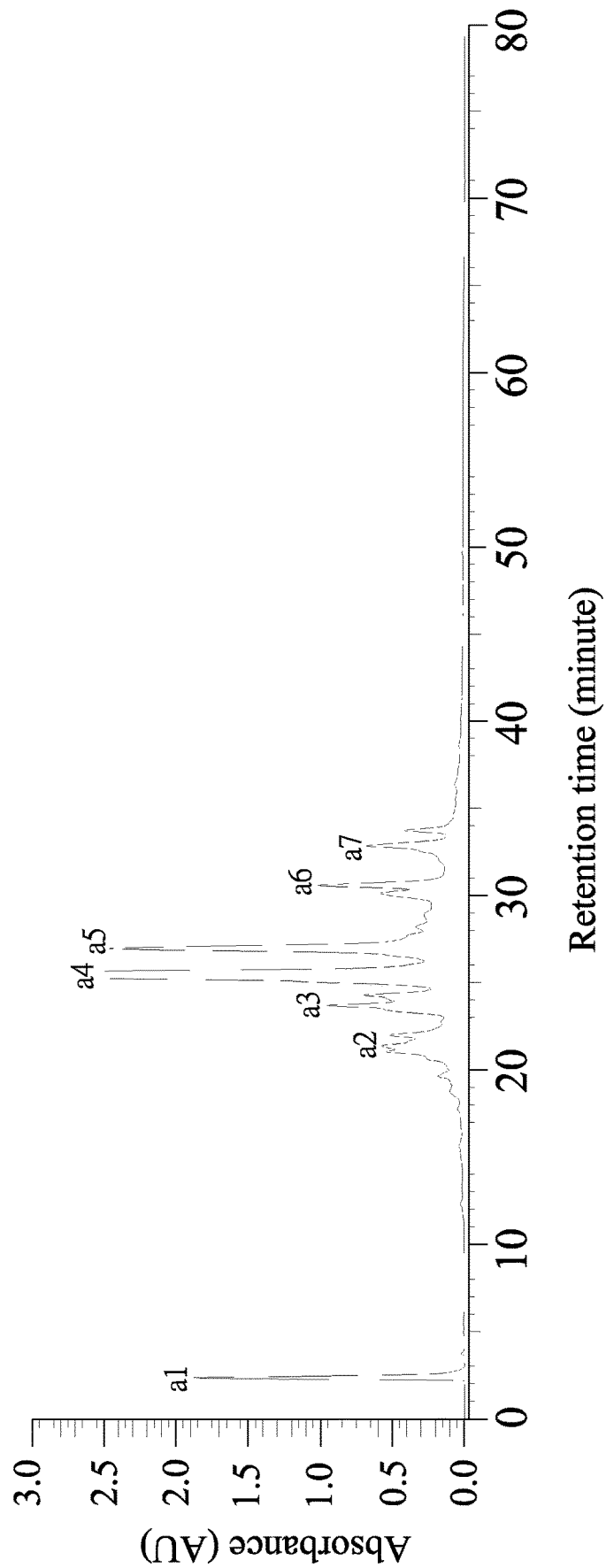
FIG. 1 is a HPLC elution profile of a first ethyl acetate-extracted product of *Sedum formosanum* prepared in Example 1, infra, in which seven peaks (respectively labeled with a1 to a7) can be detected between a retention time of 0 minute and a retention time of 80 minutes.

Unless defined otherwise, all technical and scientific terms used herein have the meaning commonly understood by a person skilled in the art to which the present disclosure belongs.

One skilled in the art will recognize many methods and materials similar or equivalent to those described herein, which could be used in the practice of the present disclosure. Indeed, the present disclosure is in no way limited to the methods and materials described. For clarity, the following definitions are used herein.

As used herein, the term "alleviating" or "alleviation" refers to at least partially reducing, ameliorating, relieving, controlling, treating or eliminating one or more clinical signs of a disease or disorder; and lowering, delaying, stopping or reversing the progression of severity regarding the condition or symptom being treated and preventing or decreasing the likelihood or probability thereof.

As used herein, the term "ultraviolet (UV) damage" refers to symptoms caused by UV overexposure to any portion of an organism (such as a human subject), which include, but are not limited to, erythema, edema, skin inflammation, UV-induced cell death, UV-induced apoptosis, delayed tanning reaction, skin aging, severe pains in the joints and muscles and around the eyes, shock, fever, nausea, vomiting, generalized weakness and skin cancer.

As used herein, the terms "skin aging" and "photoaging" can be used interchangeably, and refer to extrinsic skin aging caused by environmental factors, especially exposure of skin to UV light. The conditions of skin aging include, but are not limited to, telangiectasia, thinning of the skin, skin atrophy, decrease in collagen fiber and elastic fiber, elastosis, collagenosis, skin fibrosis, loss of skin elasticity, roughened skin texture, dryness, wrinkle formation, inflammatory cell infiltration and pigmentary change (such as lentigines, freckles, hypopigmentation or hyperpigmentation).

In this disclosure, the inventors found that an ethyl acetate-extracted product of *Sedum formosanum* has potential in alleviating UV damage. In particular, the ethyl acetate-extracted product of *Sedum formosanum* has been proven to effectively protect normal skin cells (such as human skin keratinocytes and human fetal skin fibroblast cells) against UV-induced death, UV-induced apoptosis and UV-induced skin aging. In addition, the ethyl acetate-extracted product of *Sedum formosanum* also has been proven to be capable of inhibiting the cell growth of skin cancers, especially human skin melanoma and squamous carcinoma mainly induced by UV.

Accordingly, the present disclosure provides a composition for use in alleviating UV damage, containing an ethyl acetate-extracted product of *Sedum formosanum*.

The present disclosure also provides a method for alleviating UV damage, including administering to a subject in need thereof the composition containing an ethyl acetate-extracted product of *Sedum formosanum*.

In certain embodiments, the ethyl acetate-extracted product of *Sedum formosanum* is prepared by a process including the steps of:

(a) extracting *Sedum formosanum* with a solution of monohydric alcohol to obtain a alcohol-extracted product from *Sedum formosanum*;

(b) partitioning the alcohol-extracted product with water and n-hexane to obtain an aqueous layer and a n-hexane layer; and (c) partitioning the aqueous layer obtained in step (b) with ethyl acetate, followed by collecting an ethyl acetate layer thus formed to obtain the ethyl acetate-extracted product of *Sedum formosanum*.

Examples of the monohydric alcohol suitable for use in this disclosure include, but are not limited to, methanol, ethanol, and the combination thereof. In an exemplary embodiment, the monohydric alcohol used in step (a) is methanol. In another exemplary embodiment, the monohydric alcohol used in step (a) is ethanol.

According to this disclosure, the solution of monohydric alcohol may have a concentration ranging from 70% to 100%. In certain embodiments, the solution of monohydric alcohol has a concentration ranging from 85% to 100%. In an exemplary embodiment, the solution of monohydric alcohol has a concentration ranging from 95% to 100%.

According to this disclosure, the ratio of the *Sedum formosanum* to the solution of monohydric alcohol may range from 1:5 (w/v, g/mL) to 1:15 (w/v, g/mL). In certain embodiments, the ratio of the *Sedum formosanum* to the solution of monohydric alcohol ranges from 1:8 (w/v, g/mL) to 1:12 (w/v, g/mL). In an exemplary embodiment, the ratio of the *Sedum formosanum* to the solution of monohydric alcohol is 1:10 (w/v, g/mL).

According to this disclosure, the extraction step (a) may be conducted at a temperature ranging from 30° C. to 50° C. In an exemplary embodiment, the extraction step (a) is conducted at room temperature.

In certain embodiments, the extraction with the solution of monohydric alcohol may be conducted under sonication so as to achieve the desired extraction result.

According to this disclosure, the ratio of water to n-hexane in the partition step (b) may range from 1:0.5 (v/v) to 1:5 (v/v). In certain embodiments, the ratio of water to n-hexane ranges from 1:1 (v/v) to 1:3 (v/v). In an exemplary embodiment, the ratio of water to n-hexane in the partition step (b) is 1:1 (v/v).

According to this disclosure, the partition steps (b) and/or (c) may be independently conducted at room temperature.

In certain embodiments, the extraction step (a), and the partition steps (b) and/or (c) may be repeatedly conducted so as to achieve the desired extraction result.

In certain embodiments, the UV damage to be alleviated may include one of UV-induced death of normal cells and UV-induced apoptosis of normal cells.

In an exemplary embodiment of this disclosure, the UV damage to be alleviated may include skin aging. In another exemplary embodiment of this disclosure, the UV damage to be alleviated may include skin cancer.

According to this disclosure, the skin cancer may be at least one of squamous cell carcinoma (SCC), malignant melanoma, basal cell carcinoma (BCC) and Merkel cell carcinoma (MCC).

According to the present disclosure, the composition containing the ethyl acetate-extracted product of *Sedum formosanum* may be a pharmaceutical composition that could be formulated into a suitable dosage form for parenteral, oral or topical administration using technology well known to those skilled in the art. The suitable dosage form includes, but is not limited to, injection products (e.g. sterile aqueous solutions or dispersions), sterile powder, tablets, troches, lozenges, pellets, capsules, dispersible powder or granules, solutions, suspensions, emulsions, syrup, elixir, slurry, external preparations, and the like. That is, the present disclosure is also directed to use of the abovementioned ethyl acetate-extracted product of *Sedum formosanum* in the manufacture of a pharmaceutical composition for alleviating UV damage.

The pharmaceutical composition according to the present disclosure may further include a pharmaceutically acceptable carrier widely employed in the art of drug-manufacturing. For instance, the pharmaceutically acceptable carrier may include one or more of the following agents: solvents, buffers, suspending agents, decomposers, disintegrating agents, dispersing agents, binding agents, excipients, stabilizing agents, chelating agents, diluents, gelling agents, preservatives, lubricants, absorption delaying agents, liposomes, and the like. The choice and amount of the aforesaid agents are within the expertise and routine skills of those skilled in the art.

The pharmaceutical composition according to the present disclosure may be administered via one of the following parenteral routes: intraperitoneal injection, subcutaneous injection, intramuscular injection and intravenous injection. In an embodiment of the present disclosure, the pharmaceutical composition is formulated into a suitable dosage form for subcutaneous injection.

The pharmaceutical composition according to the present disclosure can be formulated into an external preparation suitable for topical application to the skin using technology well known to those skilled in the art. The external preparation includes, but is not limited to, emulsions, gels, ointments, creams, patches, liniments, powder, aerosols, sprays, lotions, serums, pastes, foams, drops, suspensions, salves, and bandages.

According to the present disclosure, the external preparation is prepared by admixing the pharmaceutical composition with a base that is well known and commonly used in the art.

According to the present disclosure, the base may include one or more of the following additives: water, alcohols, glycols, hydrocarbons (such as petroleum jelly and white petrolatum), waxes (such as paraffin and yellow wax), preserving agents, antioxidants, surfactants, absorption enhancers, stabilizing agents, gelling agents (such as Carbopol 941, microcrystalline cellulose and carboxymethylcellulose), active agents, humectants, odor absorbers, fragrances, pH-adjusting agents, chelating agents, emulsifiers, occlusive agents, emollients, thickeners, solubilizing agents, penetration enhancers, anti-irritants, colorants, propellants, etc. The choice and amount of the aforesaid additives are within the expertise and the routine skills of those skilled in the art.

The dosage and frequency of administration of the pharmaceutical composition according to the present disclosure may vary depending on the following factors: the severity of the disease to be alleviated, the route of administration, and the age, physical condition and response of the subject to be treated. For instance, the dosage and frequency of topical administration of the pharmaceutical composition according to the present disclosure may be 0.01 mg/cm$^2$ of the skin area to 0.05 mg/cm$^2$ of the skin area, once to three times per day. The dosage and frequency of parenteral or oral administration of the pharmaceutical composition may be 25 mg/kg to 50 mg/kg, once to four times per day.

In the present disclosure, the inventors found that pretreatment of cells with the ethyl acetate-extracted product of *Sedum formosanum* is not only able to effectively protect human skin keratinocytes against UV-induced apoptosis, but also to significantly reduce UV-induced breakdown of extracellular matrix (such as collagens and elastines) in the human fetal skin fibroblast cell. Therefore, the present disclosure is directed to cosmetic use of a composition containing the ethyl acetate-extracted product of *Sedum formosanum*. That is, the composition used in the method of the present disclosure may be a cosmetic composition.

According to the present disclosure, the cosmetic composition may further include a cosmetically acceptable adjuvant that is widely employed in cosmetic-manufacturing industry. For instance, the cosmetically acceptable adjuvant may include one or more of the following reagents: solvents, gelling agents, activating agents, preservatives, antioxidants, screening agents, chelating agents, surfactants, coloring agents, thickening agents, fillers, fragrances and odor absorbents. The choice and amount of the aforesaid reagents are within the expertise and the routine skills of those skilled in the art.

The cosmetic composition provided in this disclosure may be prepared using technology well known to a skilled artisan into a form of skincare or makeup products. Such form includes, but is not limited to, aqueous solutions, aqueous-alcohol solutions or oily solutions, emulsions (oil-in-water type, water-in-oil type or complex type), gels, ointments, cream, masks, patches, packs, liniments, powder, aerosols, sprays, lotions, serums, pastes, foams, suspensions, drops, mousse, sunblock, tonic water, foundation, eyeshadow, makeup remover products, soaps and other body cleansing products.

The cosmetic composition according to the present disclosure may be used with the following external use agents: whitening agents (such as tretinoin, catechin, kojic acid, arbutin, and vitamin C), humectants, anti-inflammatory agents, bactericides, ultraviolet absorbers, plant extracts (such as aloe extract), skin nutrients, anesthetics, anti-acne agent, antipruritics, analgesics, anti-dermatitis agents, anti-hyperkeratolytic agents, anti-dry skin agents, anti-psoriatic agents, antiaging agents, anti-wrinkle agents, anti-seborrheic agents, wound-healing agents, corticosteroids, hormones, free radical scavengers (e.g., catalase), antioxidants (e.g., vitamin E), cytokines (e.g., interleukin-1), thiols (e.g., Amifostine), and steroids (e.g., 5-Androstenediol). The choice and amount of the aforesaid external use agents are within the expertise and the routine skills of those skilled in the art.

According to the present disclosure, the cosmetic composition is in a form for topical administration.

For instance, the daily dosage and frequency of topical administration of the cosmetic composition according to the present disclosure may be 1 mg/cm$^2$ of the skin area to 5 mg/cm$^2$ of the skin area, twice to five times per day.

The present disclosure will be further described in the following examples. However, it should be understood that the following examples are solely intended for the purpose of illustration and should not be construed as limiting the present disclosure in practice.

EXAMPLES

General Experimental Materials:
Source and Cultivation of Cell Lines
The cell lines used in the examples were:
(a) human skin keratinocyte cell line HaCaT and human skin melanoma cell line A375 provided by Dr. Chih-Yang Huang (Graduate Institute of Basic Medical Science, China Medical University, Taichung City, Taiwan);
(b) human fetal skin fibroblast cell line WS1 (BCRC 60300) purchased from the Bioresource Collection and Research Center of the Food Industry Research and Development Institute (BCRC of FIRDI, Taiwan); and (c) human squamous carcinoma cell line A431 provided by Dr. Chia-hsiung Cheng (Graduate Institute of Medical Sciences, Taipei Medical University, Taiwan).

Each of the cell lines were cultivated using a corresponding medium shown in Table 1 and a 6-cm Petri dish in an incubator (37° C. and 5% $CO_2$). Medium change was performed every two days. Cell passage was performed when the cultured cells reached 80%-90% of confluence.

TABLE 1

| Cell line | Medium |
|---|---|
| HaCaT and A375 | Dulbecco's Modified Eagle's Medium (DMEM) (Gibco) supplemented with 10% fetal bovine serum (FBS) (Gibco), 100 U/mL penicillin, and 100 mg/mL streptomycin (Gibco) |
| WS1 | Minimum Essential Medium Alpha medium (α-MEM) (Gibco) supplemented with 10% FBS, 100 U/mL penicillin, 100 mg/mL streptomycin, 1 mM sodium pyruvate (Gibco), and 1X MEM non-essential amino acids (NEAA) (Gibco) |
| A431 | RPMI 1640 medium (Gibco) supplemented with 10% FBS, 100 U/mL penicillin, and 100 mg/mL streptomycin |

General Experimental Procedure:
Statistical Analysis

In the following examples, each group was subjected to the same experiment three times. The experimental data are expressed as mean±standard error of the mean (SEM), and were analyzed using paired Student's t-test so as to assess the difference between all the groups. Statistical significance is indicated by $p<0.05$.

Example 1. Preparation of Ethyl Acetate-Extracted Product of *Sedum formosanum*

100 g of lyophilized powder of *Sedum formosanum* (provided by Taiwan Seed Improvement and Propagation Station, Council of Agriculture, Executive Yuan, Taiwan) was subjected to methanol extraction as follows.

The powder was mixed with 1 L of 100% methanol in a flask. The resultant mixture was subjected to sonication using an ultrasonicator (DC200H, DELTA) under a frequency of 40 kHz, and then was subjected to filtration using a Grade No. 1 Qualitative Filter Paper having a pore size of 6 μm (ADVANTEC), so as to obtain a methanol-containing filtrate.

The resulting residue from the filtration was further subjected to methanol extraction as mentioned above (i.e., mixing-sonication-filtration) three times, so as to obtain methanol-containing filtrates. The total methanol-containing filtrates thus obtained were combined and then concentrated under vacuum to remove methanol, such that a methanol-extracted product from *Sedum formosanum* was formed.

The methanol extract was dissolved in $ddH_2O$ at a ratio of 1:10 (w/v, g/mL). The solution thus formed was mixed with n-hexane (the volume ratio of $ddH_2O$ to n-hexane is 1:1), followed by subjecting the mixture to partition at room temperature for 1 hour, such that an aqueous layer and an n-hexane layer were acquired. The aqueous layer was subjected to the aforementioned partition with n-hexane thrice. The aqueous layer resulting from the last round of partition with n-hexane was mixed with ethyl acetate at a ratio of 1:1 (v/v), followed by subjecting the mixture to partition at room temperature for 1 hour, such that an aqueous layer and an ethyl acetate layer were acquired. The aqueous layer was subjected to the aforementioned partition with ethyl acetate three times. The total ethyl acetate layers thus acquired were combined and then concentrated under vacuum at 40° C. using a vacuum concentrator (Rotavapor® R II, BUCHI) to remove ethyl acetate, such that a first ethyl acetate-extracted product of *Sedum formosanum* in paste form was formed. The first ethyl acetate-extracted product was dissolved in dimethyl sulfoxide (DMSO), so as to prepare a stock solution of the first ethyl acetate-extracted product of *Sedum formosanum* having a concentration of 50 mg/mL.

In addition, a second ethyl acetate-extracted product and a stock solution thereof were prepared by procedures similar to those of the first ethyl acetate-extracted product and the stock solution thereof, except that the lyophilized powder of *Sedum formosanum* was extracted with 95% ethanol to obtain an ethanol-extracted product from *Sedum formosanum*.

Example 2. High Performance Liquid Chromatography (HPLC) Analysis for Ethyl Acetate-Extracted Product of *Sedum formosanum*

Each of the first and second ethyl acetate-extracted products of *Sedum formosanum* prepared according to the above Example 1 was dissolved in methanol to obtain a test sample having a concentration of 5 mg/mL, and then a HPLC analysis was conducted, so as to determine the major components therein.

The HPLC instruments employed areas follows: Hitachi high performance liquid chromatography system equipped with a pump (L-2130, Hitachi), a UV detector (L2400, Hitachi) and a Luna C18 column (Phenomenex, size: 150 mm×2 mm).

The operating conditions of HPLC are described as follows. The UV detector was set at a wavelength of 270 nm. Mobile phase is deionized water added with 0.1% formic acid/acetonitrile in 0.1% formic acid (90:10, v/v), and the flow rate of the mobile phase is 0.2 mL/min. Gradient elution with the mobile phase was conducted for 80 minutes as follows: the amount of acetonitrile in 0.1% formic acid was increased from 10% to 20% during 0-10 minutes, was increased from 20% to 95% during 10-45 minutes, was maintained at 95% during 45-55 minutes, was decreased from 95% to 10% during 55-60 minutes, and was maintained at 10% during 60-80 minutes.

In addition, HPLC was also conducted for the standard specimens (500 μM) of vitexin and astragalin, which were purchased from Shanghai BeiZhuo Biotechnology Co., Ltd., using the aforementioned equipments and operating conditions.

Figure 2:
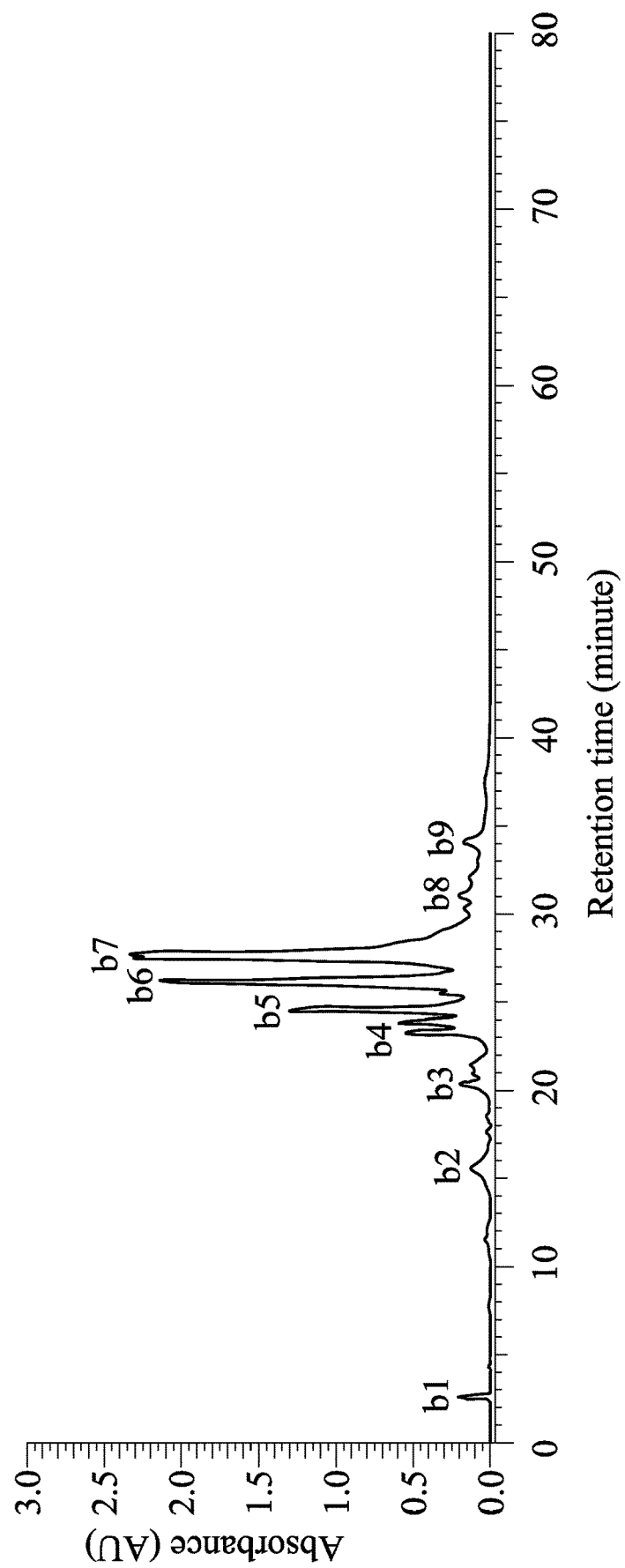
FIG. 2 is a HPLC elution profile of a second ethyl acetate-extracted product of *Sedum formosanum* prepared in Example 1, infra, in which nine peaks (respectively labeled with b1 to b9) can be detected between a retention time of 0 minute and a retention time of 80 minutes.

Results:

FIGS. 1 and 2 are HPLC elution profiles of the first and second ethyl acetate-extracted products of *Sedum formosanum* prepared in Example 1. As shown in FIGS. 1 and 2, seven major peaks (respectively labeled with a1, a2, a3, a4, a5, a6 and a7) and night major peaks (respectively labeled with b1, b2, b3, b4, b5, b6, b8 and b9) can be found respectively for the first and second ethyl acetate-extracted products between a retention time of 0 minute and a retention time of 80 minutes. In particular, the first and second ethyl acetate-extracted products have similar elution profiles between a retention time of 24 minute and a retention time of 28 minutes (i.e., peaks a3 to a5 of the first ethyl acetate-extracted product and peaks b5 to b7 of the second ethyl acetate-extracted product), where peaks a3 and b4 are identified to represent vitexin and peaks a4 and b6 are identified to represent astragalin.

Example 3. Evaluation of the Effect of the Ethyl Acetate-Extracted Product of *Sedum Formosanum* on Skin Cells with Ultraviolet (UV)-Induced Death Experimental Procedures:

A. Treatment of HaCaT Cells Using the Ethyl Acetate-Extracted Product of *Sedum formosanum* and UV Irradiation HaCaT cells were divided into 12 groups, including four control groups (i.e., normal control group and UV control groups 1-3) and eight experimental groups (i.e. experimental groups L-0 to L-3 and H-0 to H-3).

Each group of HaCaT cells was incubated in a 6-cm Petri dish containing 5 mL DMEM (supplemented with 10% FBS, 100 U/mL penicillin and 100 mg/mL streptomycin), followed by cultivation in an incubator (37° C., 5% $CO_2$) for 24 hours. After medium change with a fresh medium, the cell cultures of the eight experimental groups were treated with suitable amounts of the stock solution of the first ethyl acetate-extracted product of *Sedum formosanum* obtained in Example 1 so that the cell cultures of these experimental groups respectively had a final concentration as shown in Table 2. The cell cultures of the four control groups were not treated with the first ethyl acetate-extracted product of *Sedum formosanum*.

Afterwards, the treated HaCaT cells in each group were cultivated in an incubator (37° C., 5% $CO_2$) for 2 hours, and then subjected to UV irradiation using a CL-1000 ultraviolet crosslinker (UVP) at a dose shown in Table 2.

TABLE 2

| Groups | Final concentration of the first ethyl acetate-extracted product (μg/mL) | Dose of UV irradiation (mJ/cm²) |
| --- | --- | --- |
| Normal control group | — | — |
| UV control group 1 | — | 10 |
| UV control group 2 | — | 20 |
| UV control group 3 | — | 30 |
| Experimental group L-0 | 125 | — |
| Experimental group L-1 | | 10 |
| Experimental group L-2 | | 20 |
| Experimental group L-3 | | 30 |
| Experimental group H-0 | 250 | — |
| Experimental group H-1 | | 10 |
| Experimental group H-2 | | 20 |
| Experimental group H-3 | | 30 |

After UV irradiation, the HaCaT cells in each group were cultivated in an incubator (37° C., 5% $CO_2$) for 2 hours. The resultant cell culture was used for the following clonogenic assay.

B. Clonogenic Assay 0.5 mL of trypsin-EDTA was added to the cell culture in each group obtained above, so as to detach the cells from the surface of the Petri dish. Afterwards, 2 mL of fresh medium was added to neutralize the activity of trypsin, and the detached cells were sufficiently dispersed by virtue of repeated aspiration with a pipette. The resultant cell suspension of each group was placed in a new 6-cm Petri dish at a suitable cell number as shown in Table 3, followed by cultivation in an incubator (37° C., 5% $CO_2$) for two weeks.

TABLE 3

| Groups | Plated cell number |
| --- | --- |
| Normal control group<br>Experimental group L-0<br>Experimental group H-0 | $4.0 \times 10^2$ cells per dish |
| UV control group 1<br>Experimental group L-1<br>Experimental group H-1 | $8.0 \times 10^2$ cells per dish |
| UV control group 2<br>Experimental group L-2<br>Experimental group H-2 | $3.2 \times 10^3$ cells per dish |
| UV control group 3<br>Experimental group L-3<br>Experimental group H-3 | $6.4 \times 10^3$ cells per dish |

The resultant cell colonies in each group were fixed with 3 mL of 10% (w/v) formalin, and then the fixed cell colonies were stained with 3 mL of 1% (w/v) crystal violet at 25° C. for 30 minutes. The number of cell colonies was counted using an inverted microscope (Olympus CH40) at 100× magnification.

The plating efficiency (PE) of each group was calculated using the following formula (1):

$$A = B/C \quad (1)$$

where A=plating efficiency
B=the number of cell colonies
C=the plated cell number The survival fraction of each of the experimental groups L-0 to L-3 was calculated by dividing the plating efficiency of each group by that of the experimental group L-0. Likewise, the survival fraction of each of the experimental groups H-0 to H-3 was calculated by dividing the plating efficiency of each group by that of the experimental group H-0. In addition, the survival fraction of each of the normal control group and UV control groups 1 to 3 was calculated by dividing the plating efficiency of each group by that of the normal control group. The data thus obtained were analyzed according to the method described in the preceding section, entitled "Statistical analysis," of the "General experimental procedure".

Figure 3:
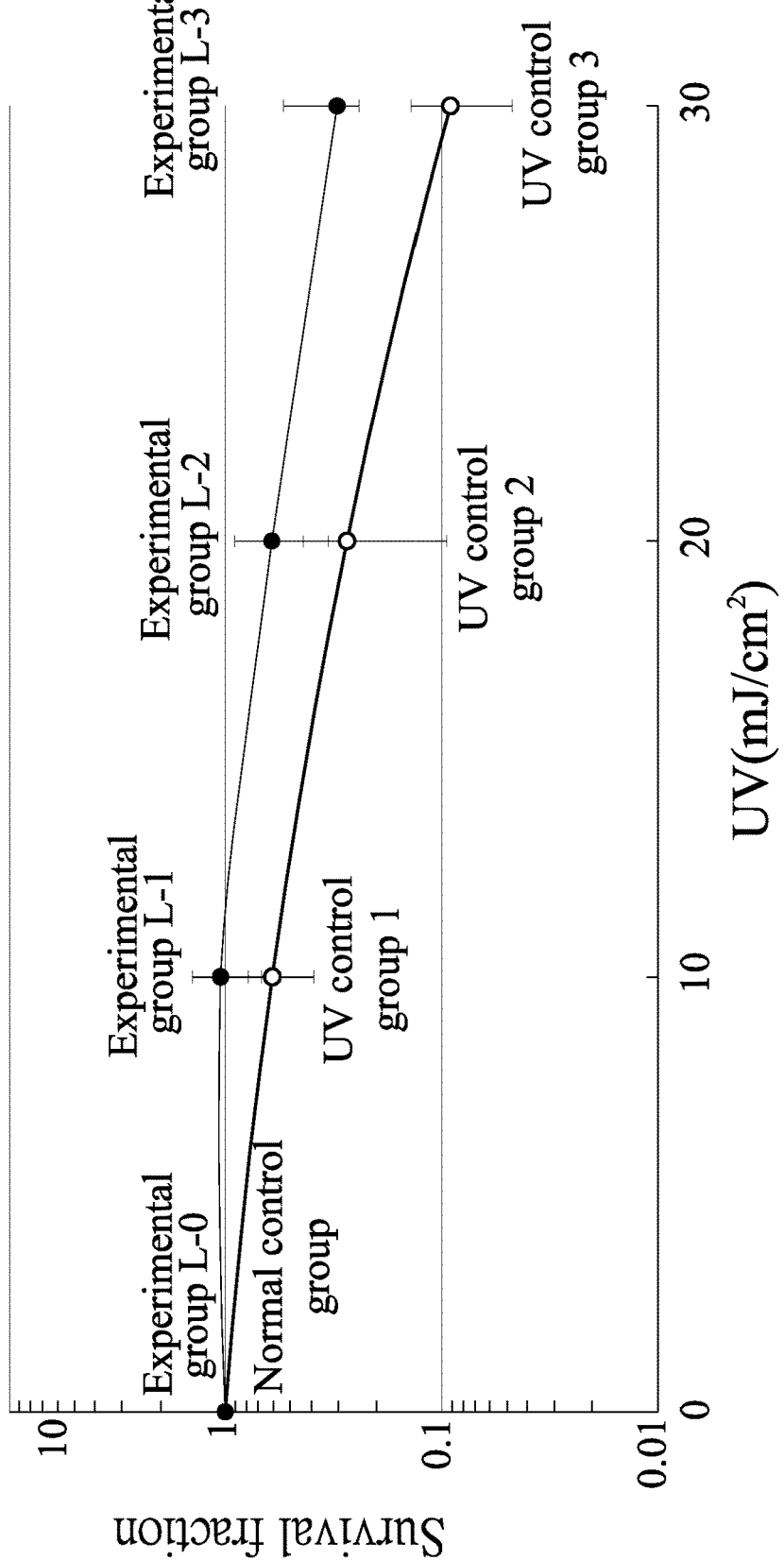
FIGS. 3 and 4 show the survival fractions of HaCaT cells in each group of Example 3, infra, as determined via clonogenic assay, in which the symbol "*" represents $p<0.05$ when compared with the respective UV control groups.
Figure 4:
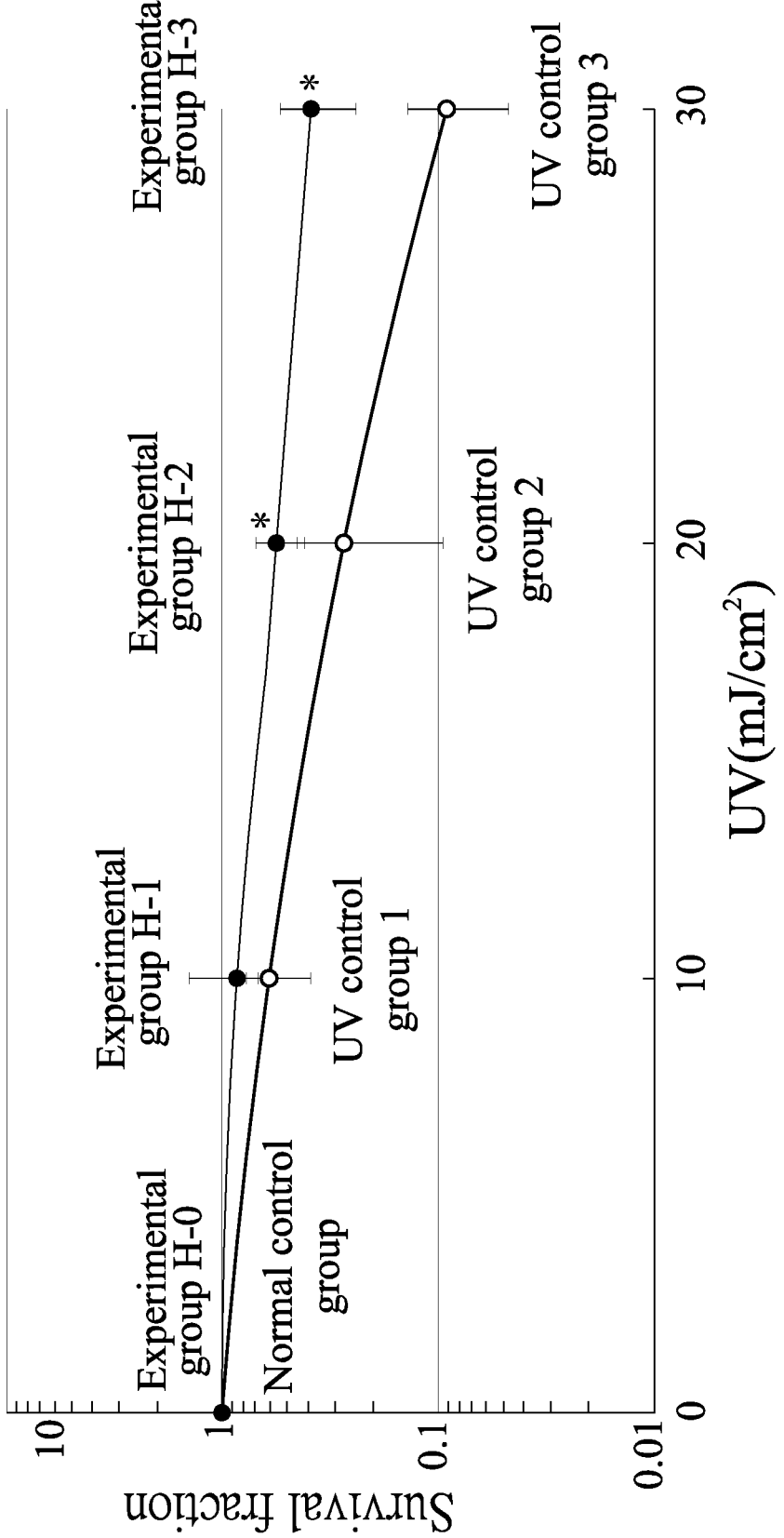

Results:

FIGS. 3 and 4 show the survival fractions of HaCaT cells in each group as determined via clonogenic assay. As shown in FIG. 3, the UV control groups 1-3 exhibit a reduction in survival fraction as compared to the normal control group, indicating that the cell growth of HaCaT cells would be inhibited by UV exposure. Similarly, the experimental groups L-2 and L-3 exhibit a reduction in survival fraction as compared to the experimental group L-0. Moreover, the experimental groups H-1 to H-3 exhibit a significant reduction in survival fraction as compared to the experimental group H-0, and such reduction becomes more apparent as the dose of UV irradiation increases (see FIG. 4). These results indicate that the cell growth of HaCaT cells would be inhibited by UV exposure.

However, under the same dose of UV exposure, the survival fraction respectively determined in the experimental groups L-1 to L-3 and H-1 to H-3 are higher than that in respective one of the UV control groups 1-3, and the survival fractions determined in the experimental groups H-1 to H-3 are also respectively higher than those determined in the experimental groups L-1 to L-3. Therefore, the applicants contemplate that the pretreatment of the ethyl acetate-extracted product of *Sedum formosanum* of this disclosure is able to protect cells against UV-induced death.

Example 4. Evaluation of the Effect of the Ethyl Acetate-Extracted Product of Sedum Formosanum on Cell Cycle Distribution of Skin Cells Experimental Procedures:

A. Treatment of HaCaT Cells Using the Ethyl Acetate-Extracted Product of *Sedum formosanum* and UV Irradiation HaCaT cells were divided into 4 groups, including two control groups (i.e., normal control group and UV control group) and two experimental groups (i.e. experimental groups L and H).

Each group of HaCaT cells was incubated in a 6-cm Petri dish containing 5 mL DMEM (supplemented with 10% FBS, 100 U/mL penicillin and 100 mg/mL streptomycin), followed by cultivation in an incubator (37° C., 5% $CO_2$) for 24 hours. After medium change with a fresh medium, the cell cultures of experimental groups L and H were treated with suitable amounts of the stock solution of the first ethyl acetate-extracted product of *Sedum formosanum* obtained in Example 1, so that the cell cultures of the experimental groups 1 and 2 respectively had a final ethyl acetate-extracted product concentration of 125 μg/mL and 250 μg/mL. The cell cultures of the two control groups were not treated with the first ethyl acetate-extracted product of *Sedum formosanum*.

The treated HaCaT cells in each group were cultivated in an incubator (37° C., 5% $CO_2$) for 2 hours. Then, the cultures in the UV control group and experimental groups 1 and 2 were subjected to UV irradiation at a dose of 50 mJ/cm$^2$. The culture in the normal control group received no UV irradiation.

After UV irradiation, the HaCaT cells in each group were cultivated in an incubator (37° C., 5% $CO_2$) for 48 hours. The resultant cell culture was subjected to the following cell cycle analysis.

B. Cell Cycle Analysis

The cell culture in each group was respectively added with 1 mL of trypsin-EDTA to detach the cells from the surface of the Petri dish. After adding 1 mL of the fresh medium to neutralize the activity of trypsin, the resultant cell suspension was subjected to centrifugation at 1200 rpm for 3 minutes. The supernatant was removed, and the cell pellet thus obtained was washed with cold PBS (pH 7.4), followed by fixing the cells with 1 mL of cold methanol. The fixed cells thus obtained were incubated at −20° C. overnight, followed by washing with cold PBS (pH 7.4). 250 μL of a cold DNA dying solution which contains 200 μg/mL RNase A solution (Sigma-Aldrich), 50 μg/mL propidium iodide (PI) (Sigma-Aldrich) and 0.1% (v/v) Triton X-100 in dd$H_2O$, was added to suspend the cells in each group. The cells were kept in the dark at 37° C. for 30 minutes to obtain stained cells.

Subsequently, the stained cells were subjected to cell cycle analysis using BD Accuri™ C6 flow cytometer (BD Biosciences), and 1.0×10$^6$ cells were analyzed in each analysis. The cells emitted fluorescence when excited by a laser beam of argon ion at 488 nm, and the fluorescence intensity was detected at a wavelength of 585 nm. The percentage of cells in each cell cycle phase was analyzed using BD Accuri™ C6 software (BD Biosciences).

Afterward, the data thus obtained were analyzed according to the method described in the preceding section, entitled "Statistical analysis," of the "General experimental procedure".

Results:

Table 4 shows the cell cycle distribution of HaCaT cells in each group.

TABLE 4

| Group | The percentage of cells in each cell cycle phase (%) | | | |
| --- | --- | --- | --- | --- |
| | Sub-G1 | G0/G1 | S | G2/M |
| Normal control group | 0.77 ± 0.17 | 56.23 ± 1.17 | 20.77 ± 0.57 | 23.43 ± 1.82 |
| UV control group | 17.17 ± 1.92** | 39.10 ± 2.49** | 14.17 ± 1.87** | 31.07 ± 4.08 |
| Experimental Group L | 9.63 ± 1.62# | 42.17 ± 1.65 | 15.23 ± 1.46 | 34.67 ± 3.76 |
| Experimental Group H | 8.23 ± 1.23## | 44.63 ± 4.83 | 11.87 ± 1.03 | 36.60 ± 6.33 |

**$p < 0.01$ when compared to the normal control group.
$p < 0.05$ when compared to the UV control group.
$p < 0.01$ when compared to the UV control group.

It can be seen from Table 4 that the cell percentage in Sub-G1 phase in the UV control group is higher than that of the normal control group, indicating that UV can induce apoptosis in HaCaT cells. In addition, the cell percentage in Sub-G1 phase in the experimental groups L and H is lower than that of the UV control group, and such lower percentage becomes more apparent as the concentration of the first ethyl acetate-extracted product of *Sedum formosanum* increases. This result suggests that the ethyl acetate-extracted product of *Sedum formosanum* according to this disclosure is effective in protecting cells against UV-induced cell death.

Example 5. Evaluation of the Effect of the Ethyl Acetate-Extracted Product of Sedum Formosanum on UV-Induced Apoptosis In this example, the applicants pretreated cells with one of the first and second ethyl acetate-extracted products of *Sedum formosanum*, astragalin or vitexin, to investigate the effect of such pretreatment on UV-induced apoptosis. Furthermore, X ray-induced apoptosis was investigated on the cells pretreated with the first ethyl acetate-extracted product of *Sedum formosanum* for comparison purpose.

Experimental Materials:

Preparation of Stock Solutions

The preparation processes of two stock solutions used in the examples are described as follows:

(1) Stock Solution of Astragalin

Astragalin (Shanghai BeiZhuo Biotechnology Co., Ltd., Cat. No. 480-10-4) was dissolved in DMSO so as to obtain a stock solution having a concentration of 4.484 mg/mL.

(2) Stock Solution of Vitexin

Vitexin (Shanghai BeiZhuo Biotechnology Co., Ltd., Cat. No. 3681-93-4) was dissolved in DMSO so as to obtain a stock solution having a concentration of 4.323 mg/mL.

Experimental Procedures:

A. Test Sample Pretreatment and Irradiation Treatment

HaCaT cells were divided into 11 groups, including three control groups (i.e., normal control group 1, UV control group 1 and X-ray control group 1), two experimental groups (i.e., experimental groups 1L and 1H) and six comparative groups (i.e., comparative groups 1L, 1H, AL, AH, VL and VH).

Each group of HaCaT cells was incubated at a cell number of $4 \times 10^5$ cells in a 6-cm Petri dish containing 5 mL DMEM (supplemented with 10% FBS, 100 U/mL penicillin and 100 mg/mL streptomycin), followed by cultivation in an incubator (37° C., 5% $CO_2$) for 24 hours. After medium change with a fresh medium, the cell cultures of the two experimental groups and six comparative groups were pretreated with the test sample so that the cell cultures of these groups respectively had a final concentration of the test sample as shown in Table 5. The cell cultures of the three control groups were not treated with any test sample.

The pretreated HaCaT cells in each group were cultivated in an incubator (37° C., 5% $CO_2$) for 2 hours. Then, the cultures in each group were subjected to X-ray irradiation using a linear accelerator (ELEKTA) or UV-irradiation using the CL-1000 ultraviolet crosslinker at a given dose shown in Table 5, except that the culture in the normal control group received no irradiation.

TABLE 5

| Groups | Final concentration of the test sample (µg/mL) | Dose of irradiation UV (mJ/cm²) | Dose of irradiation X-ray (Gy) |
|---|---|---|---|
| Normal control group 1 | — | — | — |
| UV control group 1 | — | 50 | — |
| X ray-control group 1 | — | — | 10 |
| Experimental group 1L | first ethyl acetate-extracted product | 125 | 50 | — |
| Experimental group 1H | | 250 | 50 | — |
| Comparative group 1L | | 125 | — | 10 |
| Comparative group 1H | | 250 | — | 10 |
| Comparative group AL | astragalin | 125 | 50 | — |
| Comparative group AH | | 250 | 50 | — |
| Comparative group VL | vitexin | 125 | 50 | — |
| Comparative group VH | | 250 | 50 | — |

B. Apoptosis Assay

After UV or X-ray irradiation as described in the above section A, the HaCaT cells in each group were cultivated in an incubator (37° C., 5% $CO_2$) for 48 hours. The resultant cell culture in each group was respectively added with 1 mL of trypsin-EDTA to detach the cells from the surface of the Petri dish. After adding 1 mL of fresh medium to neutralize the activity of trypsin, the resultant cell suspension was subjected to centrifugation at 1200 rpm for three minutes. The supernatant was removed, and the cell pellet thus obtained was washed once with cold PBS (pH 7.4), followed by centrifugation at 1200 rpm for 3 minutes. After removing the supernatant, the cell pellet thus obtained was sufficiently suspended with 100 µL of cold Annexin V 1X binding buffer (BD Pharmingen™), thereby obtaining a cell suspension having a cell concentration of $1.0 \times 10^6$ cells/mL. Afterward, 5 µL of FITC Annexin V (BD Pharmingen™) and 5 µL of propidium iodide (PI) staining solution (BD Pharmingen™) were added to the obtained cell suspension, followed by mixing the cell suspension evenly and incubating in the dark at 4° C. for 30 minutes.

The stained cells thus obtained were analyzed using BD Accuri™ C6 flow cytometry, in which cells stained with FITC Annexin V but not with PI (i.e., FITC Annexin V positive and PI negative) represented cells that were induced with early apoptosis; cells stained with both FITC Annexin V and PI (i.e., FITC Annexin V positive and PI positive) represented cells that were induced with late apoptosis; and cells that could not be stained with FITC Annexin V and PI (i.e., FITC Annexin V negative and PI negative) represented viable cells. The number of stained cells was calculated using BD Accuri™ C6 software.

The apoptosis percentage (%) of each group was calculated using the following formula (2):

$$D = [(E+F)/G] \times 100 \quad (2)$$

where D=apoptosis percentage (%)

E=the number of cells with PI FITC Annexin V positive and PI negative

F=the number of cells with FITC Annexin V positive and PI positive

G=the number of total cells

Afterward, the obtained data were analyzed according to the method described in the preceding section, entitled "Statistical analysis," of the "General experimental procedure".

On the other hand, the second ethyl acetate-extracted product of *Sedum formosanum* obtained in Example 1 was also used to conduct the apoptosis assay similar to that performed for the first ethyl acetate-extracted product of *Sedum formosanum*, except that each group shown in Table 6 was pretreated with a given final concentration of the second ethyl acetate-extracted product of *Sedum formosanum* and then subjected to UV irradiation at a given dose.

TABLE 6

| Groups | Final concentration of the second ethyl acetate-extracted product of *Sedum formosanum* (µg/mL) | Dose of UV irradiation (mJ/cm²) |
|---|---|---|
| Normal control group 2 | — | — |
| UV control group 2 | — | 50 |
| Experimental group 2L | 125 | 50 |
| Experimental group 2H | 250 | 50 |

C. Expression Profile of Cleaved Caspase-3

After UV or X-ray irradiation as described in the above section A, the HaCaT cells in the normal control group 1, UV control group 1 and experimental group 1H were cultivated in an incubator (37° C., 5% $CO_2$) for 24 hours. The resultant cell cultures in each group were washed with PBS twice, followed by centrifugation at 1500 rpm for 5 minutes.

After removing the supernatant, the remaining cells were added with 120 µL of a lysis buffer containing CelLytic™ M protein extraction reagent (Sigma-Aldrich) and proteinase inhibitor cocktail (Sigma-Aldrich), followed by mixing evenly and placing in 4° C. for 30 minutes. The resultant cell mixture was placed in a microcentrifuge tube, and subjected to centrifugation at 4° C. and 12000 g for 30 minutes. The supernatant thus obtained served as a total protein sample. Protein concentration in the total protein sample was determined by means of the Bio-Rad Protein Assay Kit.

The total protein sample in each group was subjected to sodium dodecyl sulfate-polyacrylamide gel electrophoresis (SDS-PAGE) analysis and Western Blotting analysis for detection of cleaved caspase-3 according to the technique well known to and routinely used by one skilled in the art. In addition, β-actin was used as an internal control.

The instruments and reagents used for SDS-PAGE analysis and Western Blotting analysis are as follows:
(1) SDS-PAGE analysis was performed using an electrophoresis system (Bio-Rad).
(2) Protein transfer was performed using a semi-dry electrophoretic transfer cell (Bio-Rad) and a polyvinylidene difluoride (PVDF) membrane.
(3) In Western Blotting analysis, primary and secondary antibodies used for detecting each protein are shown in Table 7.

TABLE 7

| Protein | Primary antibody | Secondary antibody |
| --- | --- | --- |
| Cleaved caspase-3 | Rabbit anti cleaved caspase-3 polyclonal antibody (Millipore, Cat. No. AB3623) | Goat anti rabbit IgG-horseradish peroxidase (HRP) antibody (PerkinElmer, Cat. No. SAB-300) |
| β-actin | Mouse anti β-actin monoclonal antibody (Sigma-Aldrich, Cat. No. A5441) | Goat anti mouse IgG-HRP antibody (Millipore, Cat. No. AP124P) |

(4) Chemiluminescence staining was performed using chemiluminescent HRP substrate (Millipore, Cat. No. WBKLS0500), and signal detection was performed using ImageScanner Imaging Software (GE Healthcare Life Sciences).

Subsequently, ImageScanner Imaging Software was used for semi-quantitatively calculating the corresponding protein expression level. The expression level of cleaved caspase-3 in each group was normalized by the expression level of corresponding β-actin thereof. The normalized expression level of cleaved caspase-3 in the normal group was regarded as 100%. The percentage of the normalized expression level of cleaved caspase-3 in each of the other groups relative to that in the normal control group 1 was thus calculated. Afterward, the data were analyzed according to the method described in the preceding section, entitled "Statistical analysis," of the "General experimental procedure".

Results

A. Apoptosis Assay

The apoptosis percentage in each group as determined via apoptosis assay is shown in Table 8.

TABLE 8

| Group | Apoptosis percentage (%) |
| --- | --- |
| Normal control group 1 | 2.17 ± 0.64 |
| UV control group 1 | 51.27 ± 10.17** |
| X-ray control group 1 | 27.17 ± 1.84* |
| Experimental group 1L | 12.97 ± 1.91# |
| Experimental group 1H | 6.00 ± 2.18# |
| Comparative experimental group 1L | 24.23 ± 1.61+ |
| Comparative experimental group 1H | 10.33 ± 2.17++ |
| Comparative experimental group AL | 22.37 ± 3.32 |

TABLE 8-continued

| Group | Apoptosis percentage (%) |
| --- | --- |
| Comparative experimental group AH | 69.07 ± 5.07 |
| Comparative experimental group VL | 20.00 ± 0.73 |
| Comparative experimental group VH | 70.93 ± 1.52 |
| Normal control group 2 | 2.03 ± 0.45 |
| UV control group 2 | 44.17 ± 1.16×× |
| Experimental group 2L | 29.88 ± 5.38⊛ |
| Experimental group 2H | 27.18 ± 1.26⊛⊛ |

*$p < 0.05$ when compared to the normal control group 1.
**$p < 0.01$ when compared to the normal control group 1.
$p < 0.05$ when compared to the UV control group 1.
+$p < 0.05$ when compared to the X-ray control group 1.
++$p < 0.01$ when compared to the X-ray control group 1.
××$p < 0.01$ when compared to the normal control group 2.
⊛$p < 0.05$ when compared to the UV control group 2.
⊛⊛$p < 0.01$ when compared to the UV control group 2.

As shown in Table 8, the apoptosis percentages of the UV control groups 1/2 and X-ray control group 1 are significantly higher than those of the normal control groups 1/2, indicating that both UV and X-ray can induce apoptosis in HaCaT cells. In addition, as compared to the UV control group 1, the experimental groups 1L and 1H exhibit a respective significant reduction of 74.7% and 88.3% in the apoptosis percentage (relative to that of UV control group 1), and as compared to the UV control group 2, the experimental groups 2L and 2H exhibit a respective significant reduction of 32.4% and 38.5% in the apoptosis percentage (relative to that of UV control group 2). Likewise, as compared to the X-Ray control group 1, the comparative experimental groups 1L and 1H also exhibit a respective reduction of 10.8% and 62% in apoptosis percentage (relative to that of X-ray control group 1). Such reduction becomes more apparent with the increased concentration of the first or second ethyl acetate-extracted product of *Sedum formosanum*, and the results are more remarkable for UV irradiation as compared to X-ray irradiation.

In addition, the apoptosis percentages in the comparative groups AL and VL are significantly lower than that of UV control group 1, but higher than that of the experimental group 1L. In contrast, the apoptosis percentages in the comparative groups AH and VH are significantly higher than that of UV control group 1. These results indicate that low concentration of astragalin and vitexin may protect cells from UV-induced apoptosis, but high concentration of astragalin and vitexin would aggravate the UV-induced apoptosis.

The aforesaid results show that the pretreatment of the ethyl acetate-extracted product of *Sedum formosanum* of this disclosure could effectively protect cells against X-ray-induced apoptosis and UV-induced apoptosis, and this protective effect is better for UV-induced apoptosis.

B. Expression Profile of Cleaved Caspase-3

Figure 5:
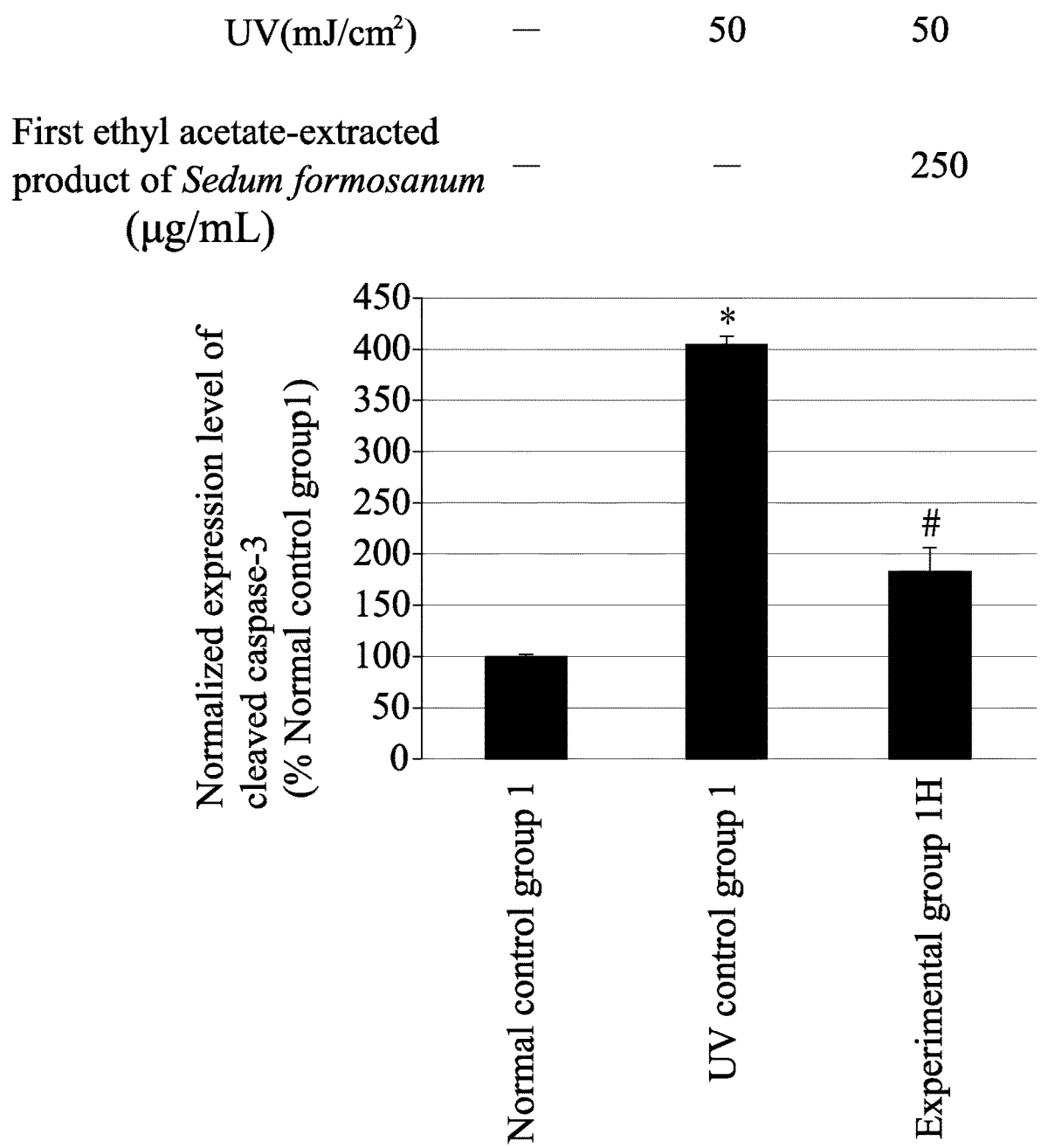
FIG. 5 shows the relative normalized expression level of cleaved caspase-3 in HaCaT cells of each group of Example 5, infra, as determined via Western Blotting analysis, in which the symbol "*" and "#" represent $p<0.05$ when respectively compared with the normal control group 1 and the UV control group 1.

FIG. 5 shows the relative normalized expression level of cleaved caspase-3 in HaCaT cells of each group as determined via Western Blotting analysis. It can be seen from FIG. 5 that as compared to the normal control group 1 (the normalized expression level of cleaved caspase-3 in the normal control group 1 was regarded as 100%), the UV control group 1 exhibits a significant increase in the normalized expression level of cleaved caspase-3, indicating that UV can induce apoptosis in HaCaT cells. In addition, the experimental group 1H exhibits a significant reduction in the normalized expression level of cleaved caspase-3 as compared to the UV control group 1. These results show that the ethyl acetate-extracted product of Sedum formosanum according to this disclosure is able to inhibit the overexpression of cleaved caspase-3 induced by UV irradiation, thereby protecting the cells against UV-induced apoptosis.

Example 6. Evaluation of the Effect of the Ethyl Acetate-Extracted Product of Sedum formosanum on UV-Induced Skin Aging In this example, the expression profiles of matrix-metalloproteinase-1 (MMP-1) and matrix-metalloproteinase-2 (MMP-2) were investigated to evaluate the protective effect of the first ethyl acetate-extracted product of Sedum formosanum according to this disclosure on UV-induced skin aging.

Experimental Procedures:

WS1 cells were divided into 3 groups, including a normal control group, a UV control group and an experimental group. Each group of WS1 cells was incubated at a cell number of $1 \times 10^6$ cells in a 10-cm Petri dish containing 10 mL α-MEM (supplemented with 10% FBS, 100 U/mL penicillin, 100 mg/mL streptomycin, 1 mM sodium pyruvate, and 1×MEM NEAA), followed by cultivation in an incubator (37° C., 5% $CO_2$) for 24 hours.

After medium change with a fresh medium, the cell culture of the experimental group was pretreated with the stock solution of the first ethyl acetate-extracted product of Sedum formosanum obtained in Example 1, so that the cell culture had a final concentration of 250 μg/mL of the same. The cell cultures of the normal control group and UV control group were not treated with the first ethyl acetate-extracted product of Sedum formosanum. After cultivating in an incubator (37° C., 5% $CO_2$) for 2 hours, the cultures in the UV control group and the experimental group were subjected to UV-irradiation using the CL-1000 ultraviolet crosslinker at a dose of 20 $mJ/cm^2$, while the culture in the normal control group received no irradiation.

Then, the WS1 cells in each group were subjected to protein expression profile analysis, which was generally conducted according to the methodas described in the section, entitled "B. Expression profile of cleaved caspase-3", of the above Example 5, except that a Western Blotting analysis using the primary and secondary antibodies as shown in Table 9 was performed to detect MMP-1 and MMP-2 expression.

TABLE 9

| Protein | Primary antibody | Secondary antibody |
| --- | --- | --- |
| MMP-1 | Rabbit anti MMP-1 polyclonal antibody (Thermo, Cat. No. PA5-27210) | Goat anti rabbit IgG-HRP antibody |
| MMP-2 | Mouse anti MMP-2 monoclonal antibody (Millipore, Cat. No. MAB3308) | Goat anti mouse IgG-HRP antibody |

Afterwards, the data were analyzed according to the method described in the preceding section, entitled "Statistical analysis," of the "General experimental procedure".

Figure 6:
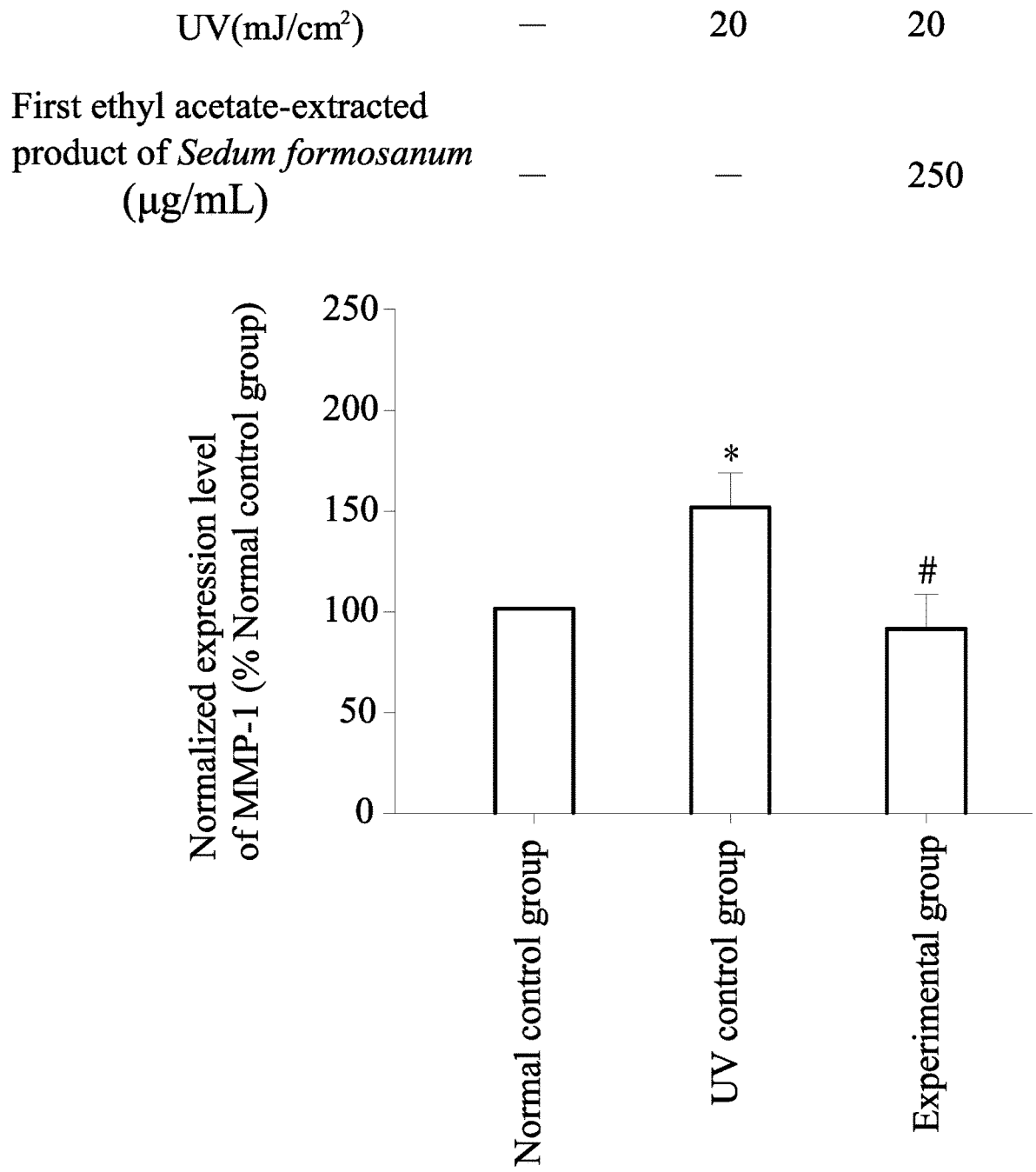
FIGS. 6 and 7 respectively show the relative normalized expression level of MMP-1 and MMP-2 in WS1 cells of each group of Example 6, infra, as determined via Western Blotting analysis, in which the symbol "*" and "#" represent $p<0.05$ when respectively compared with the normal control group and the UV control group.
Figure 7:
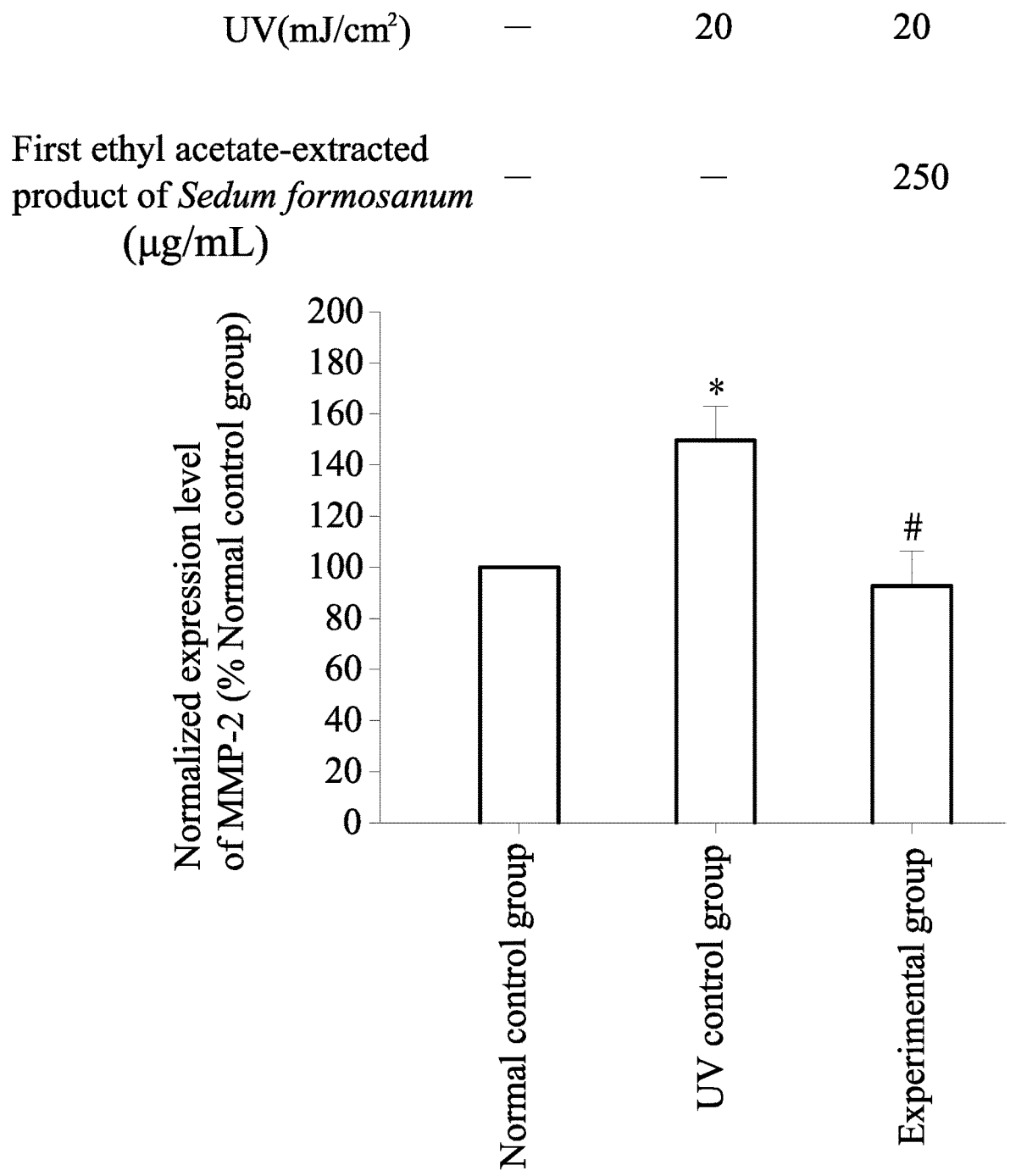

Results:

FIGS. 6 and 7 respectively show the relative normalized expression level of MMP-1 and MMP-2 in WS1 cells of each group as determined via Western Blotting analysis. It can be seen from FIGS. 6 and 7 that as compared to the normal control group (the normalized expression level of MMP-1 or MMP-2 in the normal control group was regarded as 100%), the UV control group exhibits a significant increase in the normalized expression levels of MMP-1 and MMP-2, indicating that UV can activate MMP-1 and MMP-2 to induce the degradation of collagens and elastins in WS1 cells. In addition, the experimental group exhibits a significant reduction in the normalized expression levels of MMP-1 and MMP-2 as compared to the UV control group.

These results show that the pretreatment of the ethyl acetate-extracted product of Sedum formosanum according to this disclosure can effectively inhibit overexpression of MMP-1 and MMP-2 caused by UV irradiation and the breakdown of extracellular matrix (such as collagens and elastins), thereby alleviating UV-induced skin aging.

Example 7. Evaluation of the Therapeutic Effect of the Ethyl Acetate-Extracted Product of Sedum Formosanum on Cells with UV-Induced Skin Aging In this example, the expression profiles of MMP-1 and MMP-2 were investigated to evaluate the therapeutic effect of the first ethyl acetate-extracted product of Sedum formosanum according to this disclosure on the aged skin cells induced by UV irradiation.

Experimental Procedures:

WS1 cells were divided into 3 groups, including a normal control group, a UV control group and an experimental group. Each group of WS1 cells was incubated at a cell number of $1 \times 10^6$ cells in a 10-cm Petri dish containing 10 mL α-MEM (supplemented with 10% FBS, 100 U/mL penicillin, 100 mg/mL streptomycin, 1 mM sodium pyruvate, and 1×MEM NEAA), followed by cultivation in an incubator (37° C., 5% $CO_2$) for 24 hours.

The cultures in the UV control group and the experimental group were then subjected to UV-irradiation using the CL-1000 ultraviolet crosslinker at a dose of 20 $mJ/cm^2$ to induce skin aging, while the culture in the normal control group received no irradiation.

After cultivating in an incubator (37° C., 5% $CO_2$) for 2 hours followed by medium change with a fresh medium, the cell culture of the experimental group was treated with the stock solution of the first ethyl acetate-extracted product of Sedum formosanum obtained in Example 1, so that the cell culture had a final concentration of 250 μg/mL of the same. The cell cultures of the normal control group and UV control group were not treated with the first ethyl acetate-extracted product of Sedum formosanum.

The cells were cultivated in an incubator (37° C., 5% $CO_2$) for 24 hours, and then the expression profiles of MMP-1 and MMP-2 in each group of WS1 cells were analyzed according to the method as described in the above Example 6.

Afterward, the data were analyzed according to the method described in the preceding section, entitled "Statistical analysis," of the "General experimental procedure".

Results

Figure 8:
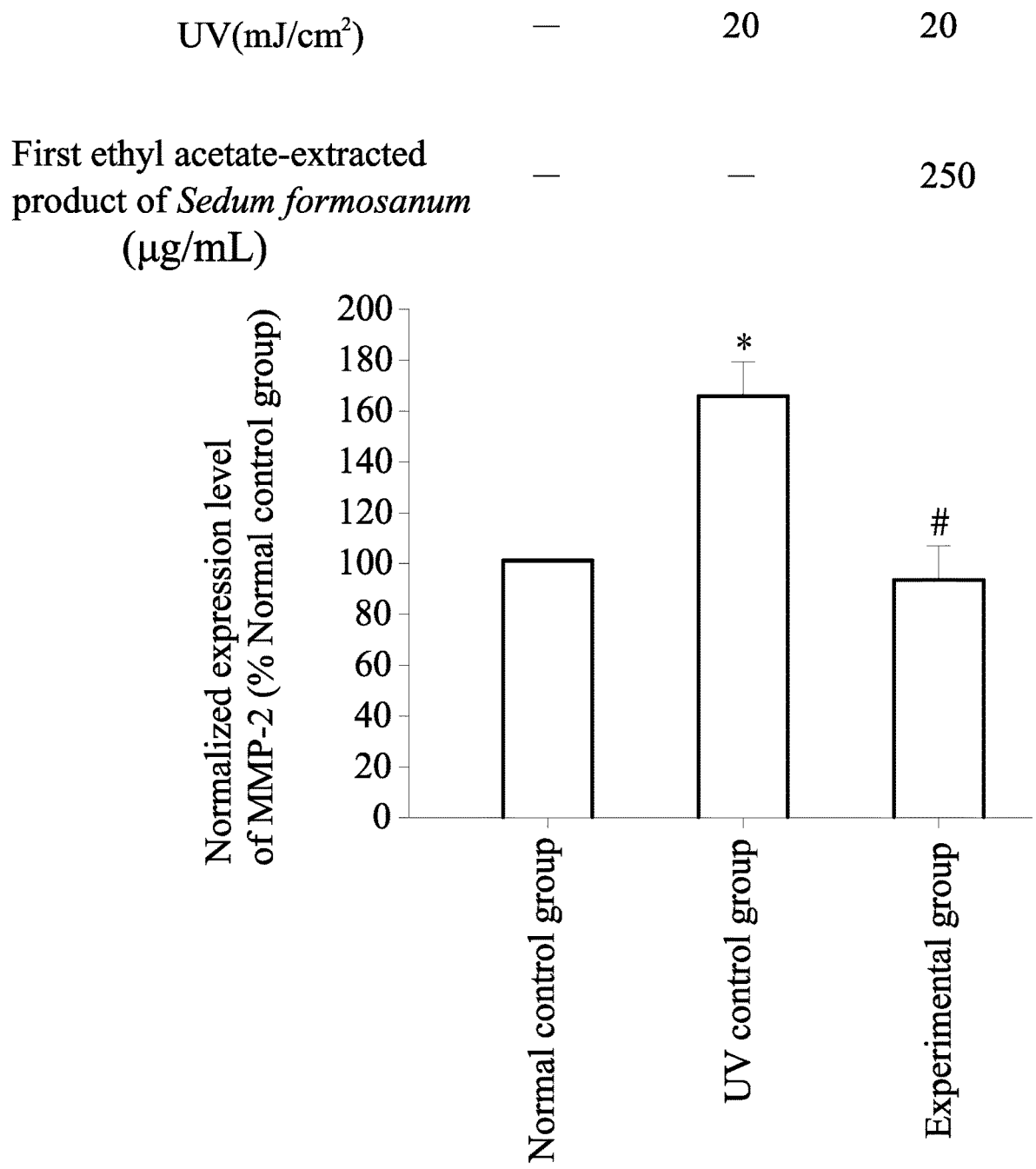
FIGS. 8 and 9 respectively show the relative normalized expression level of MMP-1 and MMP-2 in WS1 cells of each group of Example 7, infra, as determined via Western Blotting analysis, in which the symbol "*" and "#" represent $p<0.05$ when respectively compared with the normal control group and the UV control group.
Figure 9:
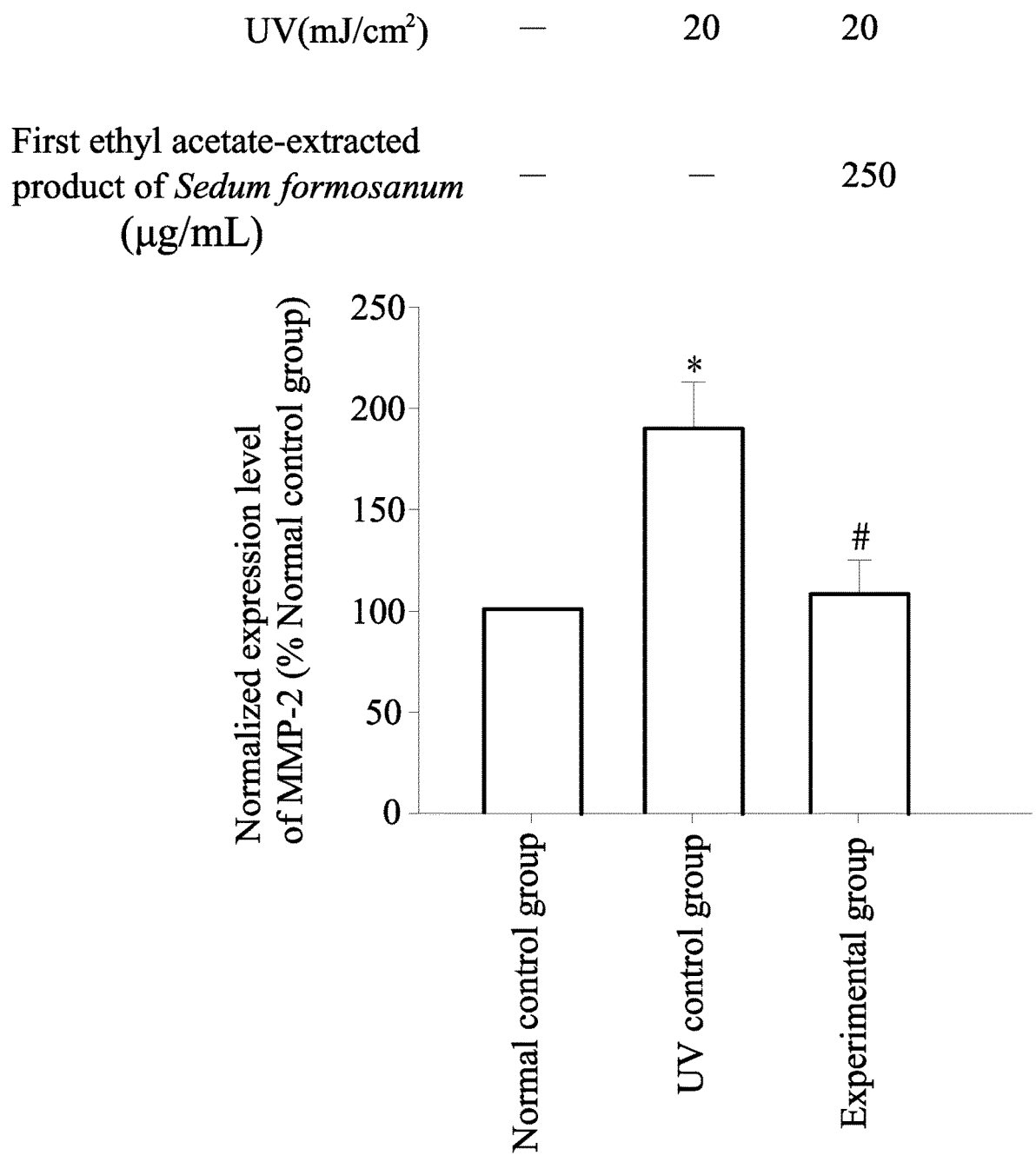

FIGS. 8 and 9 respectively show the relative normalized expression level of MMP-1 and MMP-2 in WS1 cells of each group as determined via Western Blotting analysis. It can be seen from FIGS. 8 and 9 that as compared to the normal control group (the normalized expression level of MMP-1 or MMP-2 in the normal control group was regarded as 100%), the UV control group exhibits a significant increase in the normalized expression levels of MMP-1 and MMP-2, indicating that UV can activate MMP-1 and MMP-2 to induce the degradation of collagens and elastins in WS1 cells. In addition, the experimental group exhibits a significant reduction in the normalized expression levels of MMP-1 and MMP-2 as compared to the UV control group.

These results show that the ethyl acetate-extracted product of *Sedum formosanum* according to this disclosure is capable of improving UV-induced photoaging.

Example 8. Evaluation of the Effect of the Ethyl Acetate-Extracted Product of *Sedum Formosanum* on Skin Cancer Cells In order to determine therapeutic effect of the ethyl acetate-extracted product of *Sedum formosanum* according to this disclosure on skin cancers, two cancer cell lines of the most common UV-induced skin cancers (i.e., squamous carcinoma and skin melanoma) were used in the following experiments.

Experimental Procedures:

A. Treatment of the Ethyl Acetate-Extracted Product of *Sedum formosanum*

A431 cells and A375 cells were respectively divided into a control group (i.e., A431 control group 1 and A375 control group 1) and an experimental group (i.e., A431 experimental group 1 and A375 experimental group 1).

Each group of A431 cells and A375 cells was cultured in a 6-cm Petri dish containing 5 mL of a corresponding medium as shown in Table 1 with an amount of $3\times10^5$ cells per dish, followed by cultivation in an incubator (37° C., 5% $CO_2$) for 24 hours.

After medium change with a fresh medium, the cell cultures of the A431 and A375 experimental groups 1 were respectively treated with suitable amount of the stock solution of the first ethyl acetate-extracted product of *Sedum formosanum* obtained in Example 1, so that the concentration thereof in the cell cultures is 500 μg/mL. The cell cultures of the A431 and A375 control groups 1 were not treated with the ethyl acetate-extracted product of *Sedum formosanum*.

B. Cell Cycle Analysis

A431 cells in each group and A375 cells in each group obtained in the above section A were cultivated in an incubator (37° C., 5% $CO_2$) respectively for 24 hours and 72 hours, and the resultant cell cultures were subjected to cell cycle analysis according to the method as described in the preceding section, entitled "B. Cell cycle analysis", of the above Example 4.

C. Apoptosis Assay

A431 cells in each group and A375 cells in each group obtained in the above section A were cultivated in an incubator (37° C., 5% $CO_2$) respectively for 24 hours and 72 hours, and the resultant cell cultures were subjected to apoptosis analysis according to the method as described in the preceding section, entitled "B. Apoptosis analysis", of the above Example 5.

On the other hand, the second ethyl acetate-extracted product of *Sedum formosanum* obtained in Example 1 was also used to conduct the apoptosis assay similar to that for the first ethyl acetate-extracted product of *Sedum formosanum*, except that A431 cells in each group and A375 cells in each group were treated with a given final concentration of the second ethyl acetate-extracted product of *Sedum formosanum* shown in Table 10.

TABLE 10

| Groups | Final concentration of the second ethyl acetate-extracted product of Sedum formosanum (μg/mL) |
| --- | --- |
| A431 control group 2 | — |
| A431 experimental group 2L | 250 |
| A431 experimental group 2H | 500 |
| A375 control group 2 | — |
| A375 experimental group 2L | 250 |
| A375 experimental group 2L | 500 |

D. Expression Profile of Cleaved Caspase-3

A431 cells in each group and A375 cells in each group obtained in the above section A were cultivated in an incubator (37° C., 5% $CO_2$) respectively for 24 hours and 48 hours, and the resultant cell cultures were subjected to the determination of the expression profile of cleaved caspase-3 according to the method as described in the preceding section, entitled "B. Expression profile of cleaved caspase-3", of the above Example 5.

Results:

A. Cell Cycle Analysis

Table 11 shows the distribution of A431 and A375 cells in each cell cycle phase for each group.

TABLE 11

| | The percentage of cells in each cell cycle phase (%) | | | |
| --- | --- | --- | --- | --- |
| Group | Sub-G1 | G0/G1 | S | G2/M |
| XA431 control group 1 | 5.77 ± 0.90 | 46.07 ± 0.98 | 14.20 ± 1.63 | 31.93 ± 3.78 |
| A431 experimental Group 1 | 81.30 ± 14.75* | 12.63 ± 6.96** | 3.70 ± 2.26** | 8.90 ± 5.83** |
| A375 control group 1 | 3.53 ± 0.33 | 69.93 ± 1.53 | 8.87 ± 0.65 | 16.90 ± 5.83 |
| A375 experimental Group 1 | 47.37 ± 6.97# | 12.63 ± 3.58## | 13.27 ± 6.19 | 27.60 ± 3.00# |

**$p < 0.05$ when compared to the A431 control group 1.
$p < 0.05$ when compared to the A375 control group 1.
$p < 0.01$ when compared to the A375 control group 1.

It can be seen from Table 9 that the percentages of cells in sub-G1 phase in the A431 and A375 experimental groups 1 are respectively higher than those of the A431 and A375 control groups 1. This result indicates that the ethyl acetate-extracted product of *Sedum formosanum* according to this disclosure is capable of promoting skin cancer cell death.

B. Apoptosis Assay

The apoptosis percentage of A431 and A375 cells in each group as determined via apoptosis assay is shown in Table 12.

TABLE 12

| Group | Apoptosis percentage (%) |
| --- | --- |
| A431 control group 1 | 3.33 ± 0.29 |
| A431 experimental group 1 | 55.00 ± 6.72** |
| A375 control group 1 | 0.43 ± 0.21 |
| A375 experimental group 1 | 53.50 ± 6.18## |
| A431 control group 2 | 6.67 ± 1.64 |
| A431 experimental group 2L | 39.13 ± 8.00✕ |
| A431 experimental group 2H | 75.70 ± 3.02✕✕ |
| A375 control group 2 | 1.37 ± 0.45 |
| A375 experimental group 2L | 44.17 ± 7.33☉ |
| A431 experimental group 2H | 59.27 ± 10.90☉☉ |

**$p < 0.01$ when compared to the A431 control group 1.
$p < 0.01$ when compared to the A375 control group 1.
✕$p < 0.05$ when compared to the A431 control group 2.
✕✕$p < 0.01$ when compared to the A431 control group 2.
☉$p < 0.05$ when compared to the A375 control group 2.
☉☉$p < 0.01$ when compared to the A375 control group 2.

As shown in Table 12, the apoptosis percentages of the A431 and A375 experimental groups are significantly higher than those of the A431 and A375 control groups, indicating that the ethyl acetate-extracted product of *Sedum formosanum* according to this disclosure can induce apoptosis in skin cancer cells.

C. Expression Profile of Cleaved Caspase-3

Figure 10:
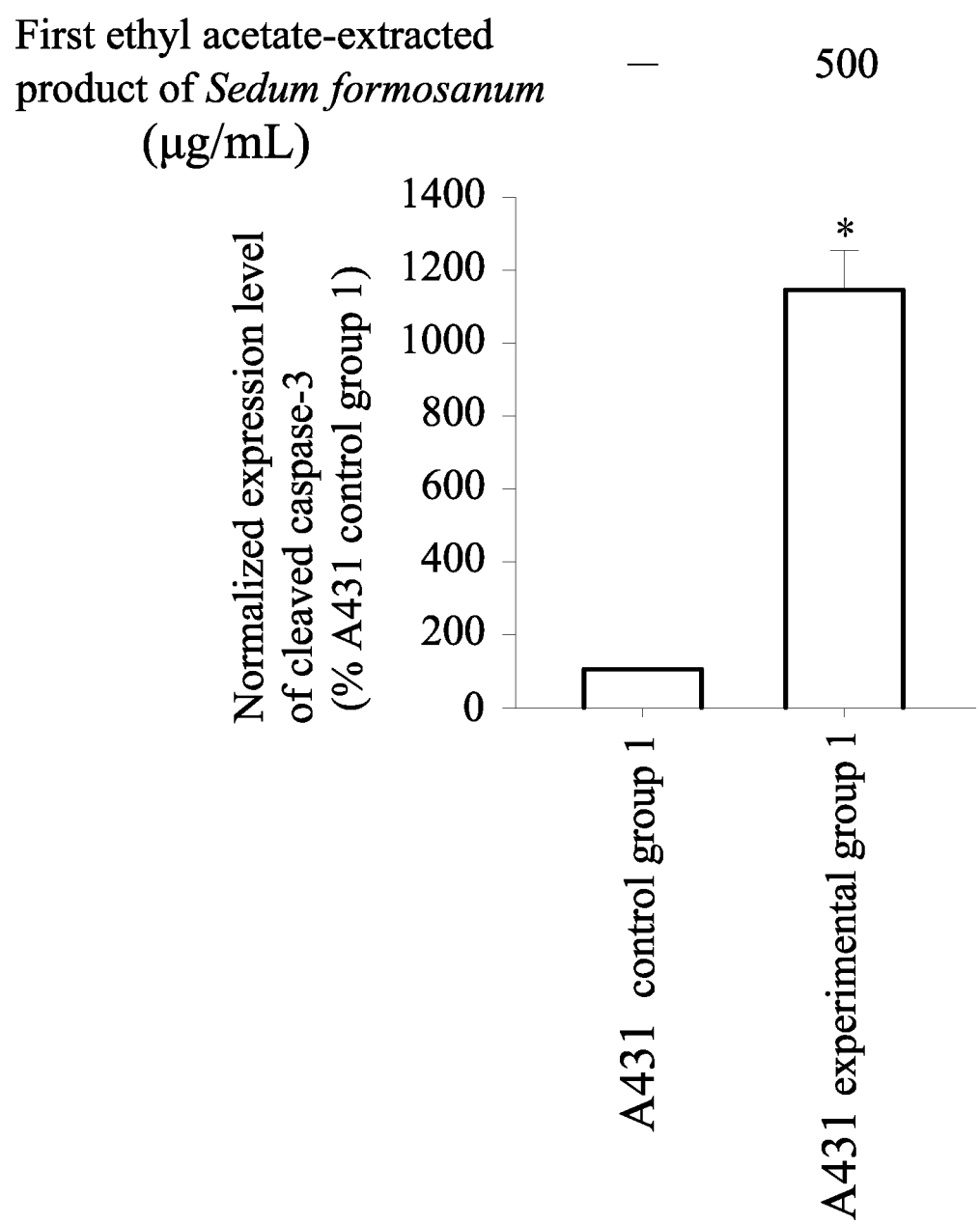
FIGS. 10 and 11 respectively show the relative normalized expression levels of cleaved caspase-3 in A431 and A375 cells of each group of Example 8, infra, as determined via Western Blotting analysis, in which the symbol "*" represents $p<0.05$ when compared with the respective control groups.
Figure 11:
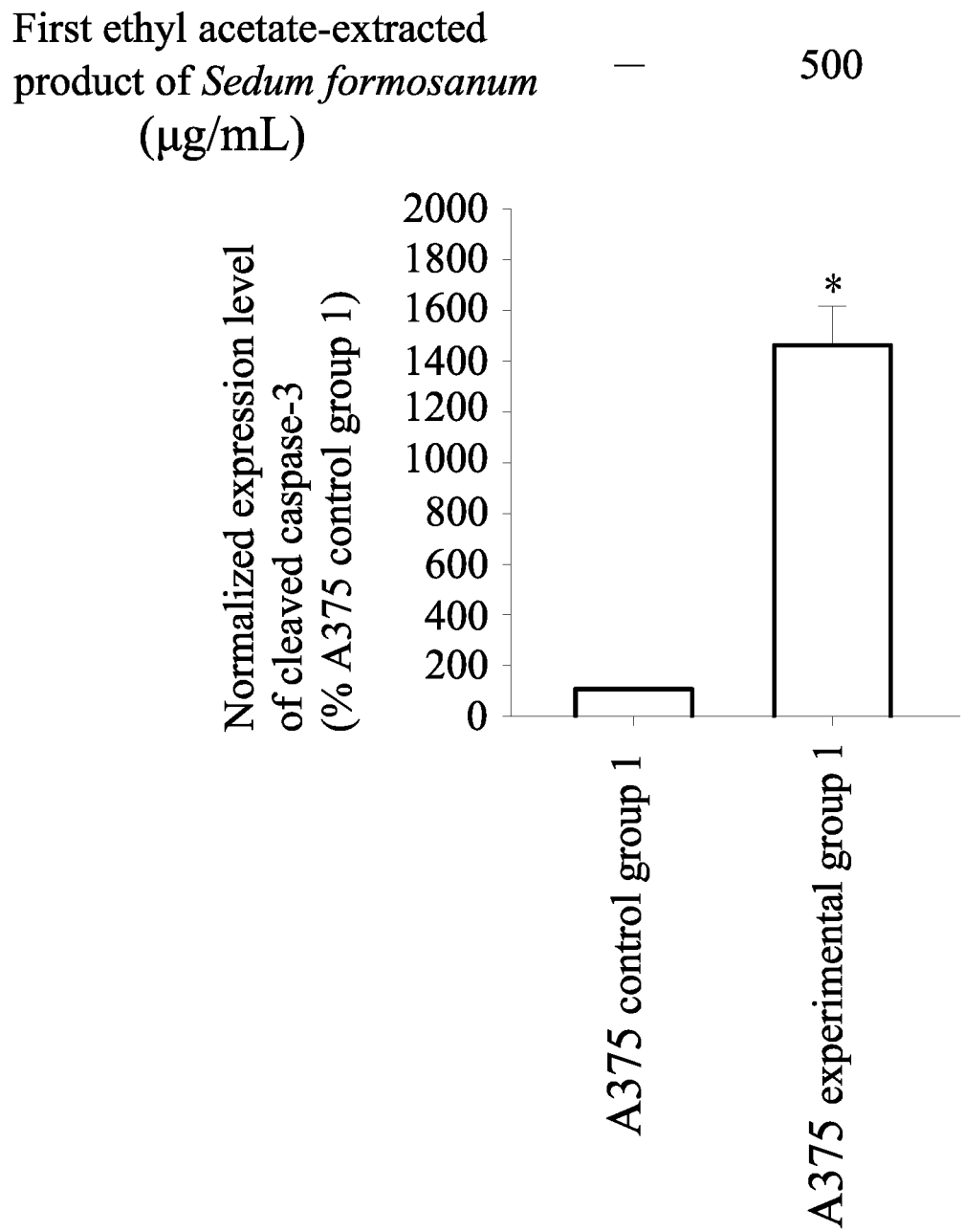

FIGS. 10 and 11 respectively show the relative normalized expression level of cleaved caspase-3 in A431 and A375 cells of each group as determined via Western Blotting analysis. It can be seen from FIGS. 10 and 11 that as compared to the A431 and A375 control groups 1 (the normalized expression level of cleaved caspase-3 in these control groups was regarded as 100%), the A431 and A375 experimental groups 1 respectively exhibit a significant increase in the normalized expression level of cleaved caspase-3, indicating that the ethyl acetate-extracted product of *Sedum formosanum* can induce apoptosis in skin cancer cells, thereby promoting cancer cell death and inhibiting cancer cell growth. Therefore, the applicants infer that the ethyl acetate-extracted product of *Sedum formosanum* according to this disclosure is capable of treating skin cancer.

Example 9. Evaluation of the Effect of the Ethyl Acetate-Extracted Product of *Sedum Formosanum* on Hairless Mice with UV-Induced Skin Aging Experimental Materials:

1. Experimental Animals:

SKH-1 hairless mice (4-5 weeks old, body weight 20±5 g) were purchased from BioLasco Taiwan Co., Ltd. The mice were kept in an animal room with an independent air conditioning system under the following laboratory conditions: a 12 hour light/12 hour dark cycle, a temperature of 24±1° C. and a relative humidity of 60±10%. Furthermore, water and feed were provided ad libitum for all experimental animals. All experiments on animals were conducted according to the Guide for the Care and Use of Laboratory Animals of National Institute of Health (NIH).

2. Test Solution:

The first ethyl acetate-extracted product of *Sedum formosanum* obtained in Example 1 was dissolved in a solution containing 35% DMSO and 65% ethanol for preparing a test solution containing 4% (w/v, g/100 mL) of the first ethyl acetate-extracted product of *Sedum formosanum* to be used in the following experiment.

Experimental Procedures:

SKH-1 hairless mice were randomly grouped into a normal control group (n=3), a UV control group (n=5) and an experimental groups (n=1). SKH-1 hairless mice in the normal control group received no UV irradiation. Dorsal skin of each of the SKH-1 hairless mice was exposed to UV irradiation three times a week for 12 weeks, using a CL-1000 ultraviolet crosslinker equipped with C8T5E UV-B lamp (302 nm), so as to induce skin aging. The single dosage of UV irradiation for each exposure is listed in Table 13.

TABLE 13

| Experimental time (week) | Single UV dosage (mJ/cm$^2$) |
| --- | --- |
| 1 | 80 |
| 2 | 160 |
| 3 | 240 |
| 4-12 | 320 |

About 2 hours prior to each exposure of UV irradiation during a 12-week experimental period, the dorsal skin of each of the mice in the experimental group was applied with the test solution obtained above at a dosage of 200 μL of the test solution per cm$^2$. The mice in the normal control group and the UV control group were not treated with the test solution.

After the 12-week experimental period, the back of each mouse was photographed, and then 1.5 cm$^3$ of dorsal skin tissue was collected using surgical scissors from the mice in each group.

The collected tissue was fixed with 10% formalin for 48 hours. The fixed tissue was embedded in paraffin and sliced to obtain a tissue section having a thickness of 4 to 6 μm.

The tissue section was subjected to Masson's staining according to the technique well known to and routinely used by one skilled in the art. The stained tissue section was examined under an optical microscope (Olympus BX41, Japan) with 100× magnification, and was photographed using a digital camera.

Figure 12:
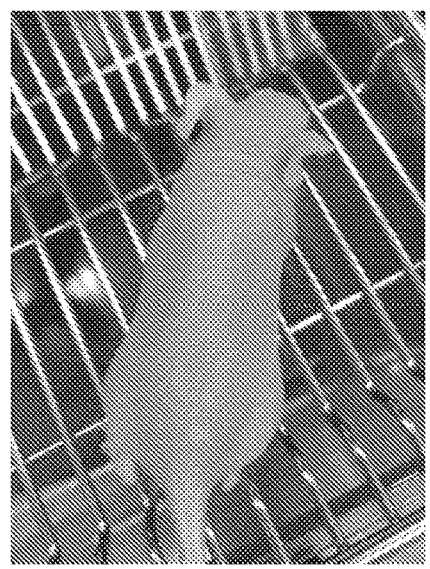
FIG. 12 shows the dorsal skin condition of the SKH-1 hairless mice in each group of Example 9, infra, after a 12-week experimental period.
Figure 12:
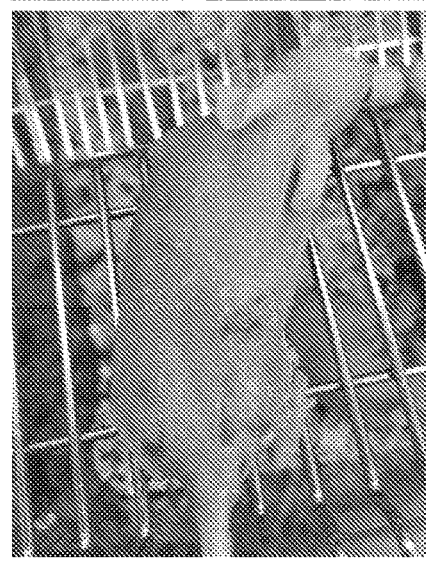
Figure 12:

Result:

FIG. 12 shows the dorsal skin condition of the SKH-1 hairless mice in each group after the 12-week experimental period. As shown in FIG. 11, the dorsal skin of the mice in the UV control group appeared thinner, swollen, with less elasticity and showed desquamation as compared to the normal control group, indicating that UV irradiation can induce skin damage. In addition, the above symptoms of skin damage in the experimental group can be significantly alleviated as compared to those in UV control group.

Figure 13:
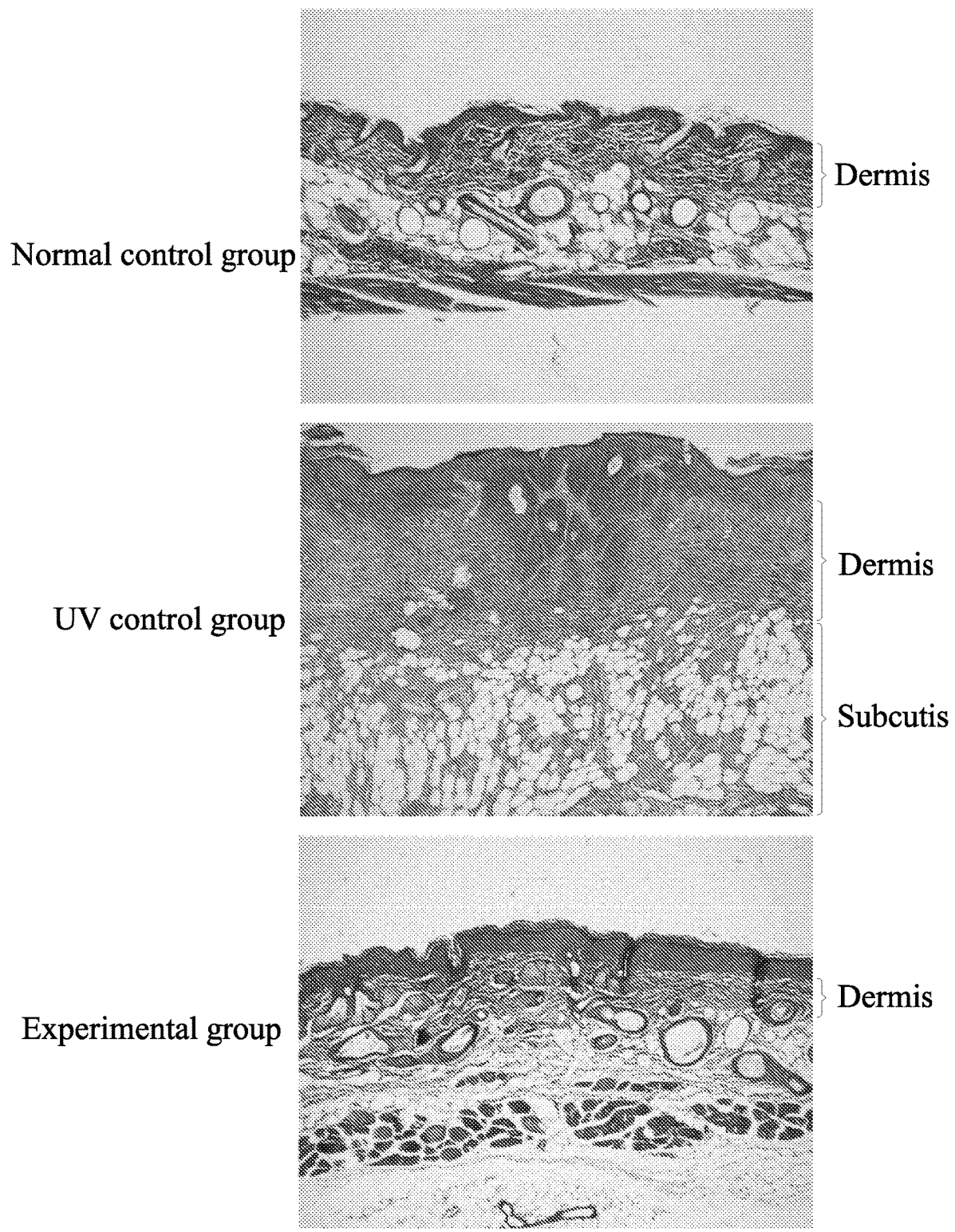
FIG. 13 shows histological images of collagenous fibers of dorsal skin tissue obtained via Masson's staining in the SKH-1 hairless mice of each group of Example 9, infra, after the 12-week experimental period.

FIG. 13 shows histological images of collagenous fibers of dorsal skin tissue obtained via Masson's staining in the SKH-1 hairless mice of each group after the 12-week experimental period. It can be seen from FIG. 13 that the collagenous fibers in the dermis of the SKH-1 hairless mouse of the normal control group were in a wave shape, but the collagenous fibers in the UV control group appeared as irregular proliferation, extending from the dermis to the subcutis. In addition, the results observed in the experimental group were similar to those of the normal control group, that is, less irregular proliferation as compared to the UV control group. These results indicate that the ethyl acetate-extracted product of *Sedum formosanum* according to this disclosure can alleviate photodamage caused by UV irradiation.

All patents and literature references cited in the present specification as well as the references described therein, are hereby incorporated by reference in their entirety. In case of conflict, the present description, including definitions, will prevail.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for alleviating ultraviolet damage, comprising administering to a subject in need thereof a composition containing an ethyl acetate-extracted product of *Sedum formosanum*.

2. The method as claimed in claim 1, wherein the ethyl acetate-extracted product of *Sedum formosanum* is prepared by a process including the steps of:

(a) extracting *Sedum formosanum* with a solution of monohydric alcohol to obtain an alcohol-extracted product from *Sedum formosanum*;

(b) partitioning the alcohol-extracted product with water and n-hexane to obtain an aqueous layer and a n-hexane layer; and (c) partitioning the aqueous layer obtained in step (b) with ethyl acetate, followed by collecting an ethyl acetate layer thus formed to obtain the ethyl acetate-extracted product of *Sedum formosanum*.

3. The method as claimed in claim 2, wherein the monohydric alcohol used in step (a) is selected from the group consisting of methanol, ethanol and the combination thereof.

4. The method as claimed in claim 1, wherein the ultraviolet damage includes photoaging.

5. The method as claimed in claim 1, wherein the ultraviolet damage includes one of UV-induced death of normal cells and UV-induced apoptosis of normal cells.

6. The method as claimed in claim 1, wherein the ultraviolet damage includes skin cancer.

7. The method as claimed in claim 1, wherein the composition is a pharmaceutical composition.

8. The method as claimed in claim 7, wherein the pharmaceutical composition further includes a pharmaceutically acceptable carrier.

9. The method as claimed in claim 7, wherein the pharmaceutical composition is in a dosage form for parenteral administration.

10. The method as claimed in claim 7, wherein the pharmaceutical composition is in a dosage form for oral administration.

11. The method as claimed in claim 7, wherein the pharmaceutical composition is in a dosage form for topical administration.

12. The method as claimed in claim 1, wherein the composition is a cosmetic composition.

13. The method as claimed in claim 12, wherein the cosmetic composition further includes a cosmetically acceptable adjuvant.

14. The method as claimed in claim 12, wherein the cosmetic composition is in a form for topical administration.

* * * * *